United States Patent [19]

Clitherow et al.

[11] 4,442,110
[45] Apr. 10, 1984

[54] 1H-1,2,4-TRIAZOLE-3,5-DIAMINE DERIVATIVES AND USE AS SELECTIVE HISTAMINE H$_2$-ANTAGONISTS

[75] Inventors: John W. Clitherow; John Bradshaw, both of Ware; John W. M. Mackinnon, Royston; Barry J. Price, Hertford; Michael Martin-Smith, Dane End, Near Ware; Duncan B. Judd, Ware, all of England

[73] Assignee: Glaxo Group Limited, London, United Kingdom

[21] Appl. No.: 324,440

[22] Filed: Nov. 24, 1981

Related U.S. Application Data

[62] Division of Ser. No. 33,508, Apr. 26, 1979, Pat. No. 4,318,913.

[30] Foreign Application Priority Data

| Apr. 26, 1978 [GB] | United Kingdom | 16468/78 |
|---|---|---|
| Dec. 8, 1978 [GB] | United Kingdom | 47689/78 |
| Mar. 2, 1979 [GB] | United Kingdom | 7907422 |

[51] Int. Cl.$^3$ .................. A01N 43/64; C07D 249/14
[52] U.S. Cl. .................................. 424/263; 424/269; 546/276; 548/267
[58] Field of Search ............... 546/210, 276; 548/267; 260/245.5; 424/267, 263, 269

[56] References Cited

U.S. PATENT DOCUMENTS

| 4,128,658 | 12/1978 | Price et al. | 424/285 |
|---|---|---|---|
| 4,239,769 | 12/1980 | Price et al. | 424/274 |

FOREIGN PATENT DOCUMENTS

| 2821410 | 11/1978 | Fed. Rep. of Germany. |
|---|---|---|
| 1419994 | 1/1976 | United Kingdom. |
| 2003471 | 3/1979 | United Kingdom. |
| 557574 | 2/1978 | U.S.S.R.. |
| 596577 | 2/1978 | U.S.S.R.. |

OTHER PUBLICATIONS

Grechishkin et al., Pharmacology 1977, vol. 15, pp. 512–518.
Grechishkin et al., Farmacol. Toksikol. 1976, vol. 39(5), pp. 556–560.

*Primary Examiner*—Henry R. Jiles
*Assistant Examiner*—Kurt G. Briscoe
*Attorney, Agent, or Firm*—Bacon & Thomas

[57] ABSTRACT

The invention relates to compounds of the general formula (I)

$$R_1R_2N-Alk-Q(CH_2)_nX(CH_2)_mNH-\underset{N}{\overset{N-N}{\underset{||}{C}}}-NR_4R_5 \quad (I)$$

and physiologically acceptable salts, hydrates and bioprecursors thereof, in which $R_1$ and $R_2$, which may be the same or different, each represent hydrogen, $C_{1-10}$ alkyl, cycloalkyl, alkenyl, alkynyl, aralkyl, trifluoroalkyl or alkyl substituted by hydroxy, alkoxy, amino, alkylamino, dialkylamino or cycloalkyl, or $R_1$ and $R_2$ may together with the nitrogen atom to which they are attached form a 5 to 10 membered alicyclic heterocyclic ring which may be saturated or may contain at least one double bond, may be unsubstituted or may be substituted by one or more $C_{1-3}$ alkyl groups or a hydroxy group and/or may contain another heteroatom;

Alk represents a straight or branched alkylene chain of 1 to 6 carbon atoms;

Q represents a furan or thiophen ring in which incorporation into the rest of the molecule is through bonds at the 2- and 5-positions, the furan ring optionally bearing a further substituent $R_7$ adjacent to the group $R_1R_2N$-Alk-, or Q represents a benzene ring in which incorporation into the rest of the molecule is through bonds at the 1- and 3- or 1- and 4- positions;

$R_7$ represents halogen or $C_{1-4}$ alkyl which may be substituted by hydroxy or $C_{1-4}$ alkoxy;

X represents —CH$_2$—, $$-\underset{\underset{R_6}{|}}{N}-,$$

—O— or —S— where
$R_6$ represents hydrogen or methyl;
n represents zero, 1 or 2;
m represents 2, 3 or 4;
$R_3$ represents hydrogen, alkyl, alkenyl, aralkyl, hydroxyalkyl having at least two carbon atoms, alkoxyalkyl or aryl; and
$R_4$ and $R_5$, which may be the same or different, each represent hydrogen, alkyl, alkyl substituted by hydroxy or $C_{1-3}$ alkoxy, alkenyl, aralkyl or heteroaralkyl or $R_4$ and $R_5$ may together with the nitrogen atom to which they are attached form a 5 to 7-membered saturated heterocyclic ring which may contain another heteroatom, or the group $$-\underset{\underset{R_6}{|}}{N}-,$$

or $R_4$ and $R_5$ taken together may represent the group =CR$_8$R$_9$ where $R_8$ represents aryl or heteroaryl and $R_9$ represents hydrogen or alkyl.

Preferably when X represents an oxygen atom or $$-\underset{\underset{R'_6}{|}}{N}-$$

and n is zero, then Q only represents a benzene ring.

The compounds of formula (I) show pharmacological activity as selective histamine H$_2$-antagonists.

21 Claims, No Drawings

1H-1,2,4-TRIAZOLE-3,5-DIAMINE DERIVATIVES AND USE AS SELECTIVE HISTAMINE H₂-ANTAGONISTS

This application is a division, of application Ser. No. 033,508, filed Apr. 26, 1979, now U.S. Pat. No. 4,318,913.

This invention relates to novel heterocyclic derivatives having action on histamine receptors, to processes for the preparation thereof, to pharmaceutical compositions containing them and to their use in therapeutics.

Certain novel heterocylic derivatives have now been found which have potent activity as H₂-antagonists. These compounds, which are more particularly described below, for example show inhibition of the secretion of gastric acid when this is stimulated via histamine receptors (Ash and Schild, Brit. J. Pharmacol. Chemother, 1966, 27, 427). Their ability to do so can be demonstrated in the perfused rat stomach using the method described in German Offenlegungsschrift No. 2,734,070, modified by the use of sodium pentobarbitone (50 mg/kg) as anaesthetic instead of urethane, and in conscious dogs equipped with Heidenhain pouches using the method described by Black et al, Nature 1972 236, 385. Furthermore the compounds antagonise the effect of histamine on the contraction frequency of isolated guinea pig right atrium but do not modify histamine induced contractions of isolated gastro-intestinal smooth muscle which are mediated via H₁-receptors. Certain compounds according to the invention have the advantage of an extended duration of action.

Compounds with histamine H₂-blocking activity may be used in the treatment of conditions where there is a hypersecretion of gastric acid, particularly in gastric and peptic ulceration, as a prophylactic measure in surgical procedures, and in the treatment of allergic and inflammatory conditions where histamine is a known mediator. Thus they may be used for example, either alone, or in combination with other active ingredients in the treatment of allergic and inflammatory conditions of the skin.

The present invention provides compounds of the general formula (I)

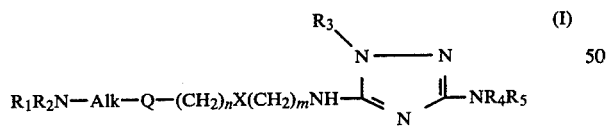

and physiologically acceptable salts, hydrates and bio-precursors thereof, in which R₁ and R₂, which may be the same or different, each represent hydrogen, $C_{1-10}$ alkyl, cycloalkyl, alkenyl, alkynyl, aralkyl, trifluoroalkyl or alkyl substituted by hydroxy, alkoxy, amino, alkylamino, dialkylamino or cycloalkyl, or R₁ and R₂ may together with the nitrogen atom to which they are attached form a 5 to 10 membered alicyclic heterocyclic ring which may be saturated or may contain at least one double bond, may be unsubstituted or may be substituted by one or more $C_{1-3}$ alkyl groups, e.g. methyl, or a hydroxy group and/or may contain another heteroatom, e.g. oxygen or sulphur, Alk represents a straight or branched alkylene chain of 1 to 6 carbon atoms, preferably 1 to 4 carbon atoms;

Q represents a furan or thiophen ring in which incorporation into the rest of the molecule is through bonds at the 2- and 5-positions, the furan ring optionally bearing a further substituent R₇ adjacent to the group

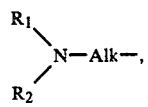

or Q represents a benzene ring in which incorporation into the rest of the molecule is through bonds at the 1- and 3- or 1- and 4-positions;

R₇ represents halogen or $C_{1-4}$ alkyl which may be substituted by hydroxy or $C_{1-4}$ alkoxy;

X represents —CH₂—,

—O— or —S— where

R₆ represents hydrogen or methyl;

n represents zero, 1 or 2;

m represents 2, 3 or 4;

R₃ represents hydrogen, alkyl, alkenyl, aralkyl, hydroxyalkyl having at least two carbon atoms, alkoxyalkyl or aryl; and R₄ and R₅, which may be the same or different, each represent hydrogen, alkyl, alkyl substituted by hydroxy or $C_{1-3}$ alkoxy, alkenyl, aralkyl or heteroaralkyl or R₄ and R₅ may together with the nitrogen atom to which they are attached form a 5 to 7-membered saturated heterocyclic ring which may contain another heteroatom, e.g. oxygen, or the group

or R₄ and R₅ taken together may represent the group =CR₈R₉ where R₈ represents aryl or heteroaryl and R₉ represents hydrogen or alkyl.

Preferably when X represents an oxygen atom or

and n is zero, then Q only represents a benzene ring.

The term 'alkyl' as a group or part of a group means that the group is straight or branched and has unless otherwise stated preferably 1 to 6 carbon atoms, and in particular 1 to 4 carbon atoms e.g. methyl or ethyl and the terms 'alkenyl' and 'alkynyl' mean that the group has preferably 3 to 6 carbon atoms. The term 'cycloalkyl' means that the group has 3 to 8 carbon atoms. The term 'aryl' as a group or part of a group preferably means phenyl or substituted phenyl, for example phenyl substituted with one or more $C_{1-3}$ alkyl or $C_{1-3}$ alkoxy groups or halogen atoms. The term 'heteroaryl' as a group or part of a group preferably means pyridyl or substituted pyridyl, e.g. pyridyl substituted with one or more $C_{1-3}$ alkyl groups.

According to one aspect the invention provides compounds of the formula (I) and physiologically acceptable salts, hydrates and bioprecursors thereof, in which $R_1$ and $R_2$, which may be the same or different, each represent hydrogen, $C_{1-6}$ alkyl, cycloalkyl, $C_{3-6}$ alkenyl, aralkyl or $C_{1-6}$ alkyl substituted by alkoxy, alkylamino or dialkylamino, or $R_1$ and $R_2$ may together with the nitrogen atom to which they are attached form a 5 to 10 membered alicyclic heterocyclic ring which may contain oxygen;

Alk represents a straight or branched alkylene chain of 1 to 6 carbon atoms;

Q represents a furan or thiophen ring in which incorporation into the rest of the molecule is through bonds at the 2- and 5-positions, the furan ring optionally bearing a further substituent $R_7$ adjacent to the group $R_1R_2N$-Alk-, or Q represents a benzene ring in which incorporation into the rest of the molecule is through bonds at the 1- and 3-positions;

$R_7$ represents $C_{1-4}$ alkyl which may be substituted by hydroxy or $C_{1-4}$ alkoxy;

X represents $-CH_2-$, $-O-$ or $-S-$;

n represents zero, 1 or 2;

m represents 2, 3 or 4;

$R_3$ represents hydrogen, $C_{1-6}$ alkyl, $C_{3-6}$ alkenyl, hydroxyalkyl having at least two carbon atoms, alkoxyalkyl, aryl or aralkyl; and $R_4$ and $R_5$, which may be the same or different, each represent hydrogen or $C_{1-6}$ alkyl;

with the proviso that when Q represents a furan, substituted furan or thiophen ring system and X represents oxygen, n cannot be zero.

The invention includes the compounds of formula (I) in the form of physiologically acceptable salts with inorganic and organic acids. Particularly useful salts include hydrochlorides, hydrobromides and sulphates; acetates, maleates, succinates, citrates and fumarates. The compounds of formula (I) and their salts may also form hydrates, which hydrates are also to be considered as part of the invention. The compounds of formula (I) can exhibit tautomerism and the formula is intended to cover all tautomers. Where optical isomers may exist the formula is intended to cover all diastereoisomers and optical enantiomers.

The compounds according to the invention, preferably in the form of a salt, may be formulated for administration in any convenient way and the invention includes within its scope pharmaceutical compositions containing at least one compound according to the invention adapted for use in human or veterinary medicine. Such compositions may be formulated in a conventional manner using one or more pharmaceutically acceptable carriers or excipients. Such compositions may also contain if required other active ingredients, e.g. $H_1$-antagonists.

Thus the compounds according to the invention may be formulated for oral, buccal, topical, parenteral or rectal administration. Oral administration is preferred.

For oral administration, the pharmaceutical composition may take the form of for example, tablets, capsules, powders, solutions, syrups or suspensions prepared by conventional means with acceptable excipients. For buccal administration the composition may take the form of tablets or lozenges formulated in conventional manner.

The compounds of the invention may be formulated for parenteral administration by bolus injection or continuous infusion. Formulations for injection may be presented in unit dosage form in ampoules, or in multidose containers, with an added preservative. The compositions may take such forms as suspensions, solutions or emulsions in oily or aqueous vehicles, and may contain formulatory agents such as suspending, stabilising and/or dispersing agents. Alternatively, the active ingredient may be in powder form for reconstitution with a suitable vehicle, e.g. sterile pyrogen-free water before use.

The compounds of the invention may also be formulated in rectal compositions such as suppositories or retention enemas, e.g. containing conventional suppository bases such as cocoa butter or other glyceride.

For topical application, the compounds of the invention may be formulated as ointments, creams, gels, lotions, powders or sprays. Ointments and creams may, for example, be formulated with an aqueous or oily base with the addition of suitable pharmaceutical excipients. Lotions may be formulated with an aqueous or oily base and will include the necessary adjustments to ensure pharmaceutically acceptable products. Spray compositions may, for example, be formulated as aerosols which may be pressurised by means of a suitable agent such as dichlorofluoromethane or trichlorofluoromethane or may be delivered by means of a hand-operated atomizer.

For internal administration a convenient daily dosage regime of the compounds according to the invention would be 1 to 6 doses to the total of some 5 mg to 2 g per day, preferably 5 to 500 mg per day.

In the compounds according to the invention, preferably the total of m+n is 3 or 4, more preferably 3.

When X is sulphur, n is preferably 1 and m is preferably 2. When X is oxygen or $$-N-,$$
$$\phantom{-N}|$$
$$\phantom{-N}R_6$$

n is preferably zero and m is preferably 3 or 4, more preferably 3.

Preferably Q is a furan ring optionally substituted by the group $R_7$, where $R_7$ represents $C_{1-3}$ alkyl optionally substituted by alkoxy or is a benzene ring in which incorporation into the rest of the molecule is through bonds at the 1- and 3- or 1- and 4-positions.

Preferably Alk represents a methylene, ethylene or propylene group.

Preferably $R_1$ represents hydrogen or $C_{1-4}$ alkyl and $R_2$ represents $C_{3-5}$ alkenyl or alkynyl, $C_{5-7}$ cycloalkyl, benzyl, $C_{1-8}$ alkyl, or $C_{1-4}$ alkyl substituted by $C_{1-3}$ alkoxy, hydroxy, $diC_{1-3}$alkylamino or trifluoromethyl or $R_1$ and $R_2$ together with the nitrogen atom to which they are attached form an alicyclic heterocyclic ring with 5 to 8 members and optionally containing one double bond and/or substituted by hydroxy or one or two $C_{1-3}$ alkyl group(s).

Preferably $R_3$ represents hydrogen or $C_{1-4}$ alkyl or hydroxyalkyl.

Preferably $R_4$ represents hydrogen or $C_{1-5}$ alkyl optionally substituted by a phenyl, pyridyl, hydroxy or $C_{1-3}$ alkoxy group and $R_5$ represents hydrogen or $C_{1-3}$ alkyl or $R_4$ and $R_5$ together with the nitrogen atom to which they are attached represent a $C_{5-7}$ saturated heterocyclic ring or $R_4$ and $R_5$ together represent the group =CHR$_8$ where R$_8$ represents a phenyl or pyridyl group.

Where R$_1$ and R$_2$ together with the nitrogen atom to which they are attached form a heterocyclic ring this ring may be pyrrolidine, piperidine optionally substituted in the 4-position by C$_{1-3}$ alkyl or hydroxy, tetrahydropyridine, morpholine, 2,6-dialkylmorpholine, hexamethyleneimine or heptamethyleneimine.

When Q represents a furan or substituted furan ring, preferably Alk represents a methylene group, R$_1$ and R$_2$ both represent C$_{1-3}$ alkyl groups and when present R$_7$ preferably represents a C$_{1-3}$ alkyl group optionally substituted with a C$_{1-3}$ alkoxy group n is 1, X is sulphur and m is 2. More preferably Q represents a substituted furan group in which R$_7$ represents a C$_{1-3}$ alkyl group, in particular methyl, which may optionally be substituted with a C$_{1-3}$ alkoxy group, in particular a methoxy group.

When Q represents a benzene ring preferably Alk represents a methylene, ethylene or propylene group; n is zero; X is oxygen or NH; m is 3 or 4; R$_1$ represents hydrogen or C$_{1-4}$ alkyl; R$_2$ represents a straight chain C$_{1-7}$ alkyl group which may be branched by a methyl group, or a C$_{1-4}$ alkyl group substituted by a di(C$_{1-3}$) alkylamino, C$_{1-3}$ alkoxy, trifluoromethyl or phenyl group or R$_2$ represents a C$_{5-7}$ cycloalkyl group or a C$_{3-5}$ alkenyl group or R$_1$ and R$_2$ together with the nitrogen atom to which they are attached form a 5 to 8 membered alicyclic heterocyclic ring which may be saturated or contain at least one double bond, or be saturated and substituted by one or more C$_{1-3}$ alkyl e.g. methyl groups and may contain an additional heteroatom e.g. oxygen; R$_3$ is H or C$_{1-2}$ alkyl or hydroxyethyl; R$_4$ represents hydrogen or C$_{1-3}$ alkyl optionally substituted by a phenyl or pyridyl group and R$_5$ represents hydrogen or C$_{1-3}$ alkyl or R$_4$ and R$_5$ together represent the group =CHR$_8$ where R$_8$ is phenyl or pyridyl.

More preferably when Q represents benzene, R$_1$ and R$_2$ represent C$_{1-3}$ alkyl, e.g. methyl, or R$_1$ represents hydrogen and R$_2$ represents C$_{1-7}$ alkyl, e.g. methyl, propyl, butyl, secondary butyl and n-heptyl, or C$_{3-5}$ alkenyl, e.g. allyl or C$_{5-7}$ cycloalkyl, e.g. cyclohexyl, or R$_1$ and R$_2$ together with the nitrogen atom to which they are attached represent a 5 to 7 membered alicyclic heterocyclic ring which may be saturated, or contain a double bond, or be saturated and substituted by one C$_{1-3}$ alkyl group e.g. methyl, in particular pyrrolidine, piperidine optionally substituted in the 4-position by a methyl group; or tetrahydropyridine or hexamethyleneimine; R$_3$ represents hydrogen, methyl, ethyl or hydroxyethyl; R$_4$ and R$_5$ both represent hydrogen or ethyl or R$_4$ and R$_5$ together represent the group =CHR$_8$ where R$_8$ represents phenyl or 4-pyridyl. Particularly, preferred compounds in which Q is benzene are those in which it is incorporated into the rest of the molecule through bonds at the 1 and 3 positions and in which Alk represents methylene, n is zero, X is oxygen and m is 3.

Particularly preferred compounds of the invention are those in which R$_3$ represents methyl and R$_4$ and R$_5$ represent hydrogen.

Particularly preferred compounds are:
(1) 1-methyl-N$^5$-[3-[3-[1-piperidinylmethyl]phenoxy]propyl]-1H-1,2,4-triazole-3,5-diamine
(2) 1-methyl-N$^5$-[3-[3-[1-pyrrolidinylmethyl]phenoxy]propyl]-1H-1,2,4-triazole-3,4-diamine
(3) 1-methyl-N$^5$-[3-[3-[1-hexamethyleneiminylmethyl]phenoxy]propyl]-1H-1,2,4-triazole-3,5-diamine
(4) N$^3$-[3-[3-(1-piperidinylmethyl)phenoxy]propyl]-1H-1,2,4-triazole-3,5-diamine
(5) 1-methyl-N$^5$-[3-[3-[(dimethylamino)methyl]phenoxy]propyl]-1H-1,2,4-triazole-3,5-diamine
(6) 1-methyl-N$^3$-phenylmethylene-N$^5$-[3-[3-[(dimethylamino)methyl]phenoxy]propyl]-1H-1,2,4-triazole-3,5-diamine
(7) 1-methyl-N$^3$-(4-pyridinylmethylene)-N$^5$-[3-[3-[(dimethylamino)methyl]phenoxy]propyl]-1H-1,2,4-triazole-3,5-diamine
(8) 1-methyl-N$^5$-[2-[[[5-(dimethylamino)methyl-4-methyl-2-furanyl]methyl]thio]ethyl]-1H-1,2,4-triazole-3,5-diamine
(9) 1-methyl-N$^5$-[3-[3-[(dimethylamino)ethyl]phenoxy]propyl]-1H-1,2,4-triazole-3,5-diamine
(10) 1-methyl-N$^5$-[3-[3-[(1-propylamino)methyl]phenoxy]propyl]-1H-1,2,4-triazole-3,5-diamine
(11) 1-methyl-N$^5$-[3-[3-[1-(1,2,3,6-tetrahydropyridinyl)methyl]phenoxy]propyl]-1H-1,2,4-triazole-3,5-diamine
(12) 1-methyl-N$^5$-[2-[[4-methoxymethyl-5-[(dimethylamino)methyl]-2-furanylmethyl]thio]ethyl]-1H-1,2,4-triazole-3,5-diamine
(13) 1-methyl-N$^5$-[3-[4-[3-(dimethylamino)propyl]phenoxy]propyl]-1H-1,2,4-triazole-3,5-diamine
(14) 1-ethyl-N$^5$-[3-[3-(1-piperidinylmethyl)phenoxy]propyl]-1H-1,2,4-triazole-3,5-diamine
(15) 1-methyl-N$^3$-diethyl-N$^5$-[3-[3-[(dimethylamino)methyl]phenoxy]propyl]-1H-1,2,4-triazole-3,5-diamine
(16) 1-methyl-N$^5$-[4-[3-(1-piperidinylmethyl)phenoxy]butyl]-1H-1,2,4-triazole-3,5-diamine
(17) 1-methyl-N$^5$-[3-[3-[1-(4-methylpiperidinyl)methyl]phenoxy]propyl]-1H-1,2,4-triazole-3,5-diamine
(18) 1-methyl-N$^5$-[3-[3-[(cyclohexylamino)methyl]phenoxy]propyl]-1H-1,2,4-triazole-3,5-diamine
(19) 1-methyl-N$^5$-[3-[3-[(2-propen-1-amino)methyl]phenoxy]propyl]-1H-1,2,4-triazole-3,5-diamine
(20) 1-methyl-N$^5$-[3-[3-[(heptylamino)methyl]phenoxy]propyl]-1H-1,2,4-triazole-3,5-diamine
(21) 1-methyl-N$^5$-[3-[3-[(2-methylpropylamino)methyl]phenoxy]propyl]-1H-1,2,4-triazole-3,5-diamine
(22) 1-methyl-N$^5$-[3-[3-[(2,2,2-trifluoroethylamino)methyl]phenoxy]propyl]-1H-1,2,4-triazole-3,5-diamine
(23) 1-methyl-N$^5$-[3-[3-[(butylmethylamino)methyl]phenoxy]propyl]-1H-1,2,4-triazole-3,5-diamine
(24) 1-(2-hydroxyethyl)-N$^5$-[3-[3-[(dimethylamino)methyl]phenoxy]propyl]-1H-1,2,4-triazole-3,5-diamine
(25) 1-(2-hydroxyethyl)-N$^5$-[3-[3-[(1-piperidinylmethyl)phenoxy]propyl]-1H-1,2,4-triazole-3,5-diamine
and their physiologically acceptable salts.

Of the above mentioned compounds, compound Nos. (1), (2), (3) and (4) and their salts are particularly preferred.

It will be appreciated in the methods for the preparation of compounds of formula (I) given below, that for certain reaction steps it may be necessary to protect various reactive substituents in the starting materials for a particular reaction and subsequently to remove the protecting group. Such protection and subsequent deprotection may be particularly pertinent where R$_1$ and/or R$_2$ in intermediates used to prepare compounds of formula (I) are hydrogen atoms and/or when R$_3$ in intermediates is an alkyl group bearing a hydroxy substituent and/or when R$_4$ and/or R$_5$ in certain intermediates are hydrogen atoms. Standard protection and deprotection procedures can be employed:

for example formation of phthalimide (in the case of primary amines), benzyl, benzyloxycarbonyl, or trichloroethoxycarbonyl derivatives. Subsequent cleavage of the protecting group is achieved by conventional procedures. Thus a phthalimide group may be cleaved by treatment with a hydrazine e.g. hydrazine hydrate or a primary amine for example methylamine; benzyl or benzyloxycarbonyl derivatives may be cleaved by hydrogenolysis in the presence of a catalyst, e.g. palladium, and trichloroethoxycarbonyl derivatives may be cleaved by treatment with zinc dust.

Compounds according to the invention in which $R_4$ and $R_5$ are hydrogen can be prepared by cyclising a compound of formula (II)

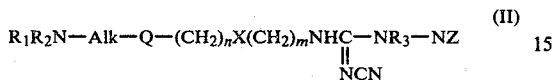

in which $R_1$, $R_2$, Alk, Q, n, X, m and $R_3$ are as defined in formula (I) or are groups convertible thereto and Z represents two hydrogen atoms. In carrying out the above reaction it is convenient to prepare compounds of formula (I) in which $R_4$ and $R_5$ are both hydrogen by reacting a compound of formula (III)

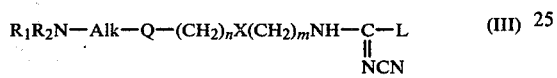

in which $R_1$, $R_2$, Alk, Q, n, X, and m are as defined in formula (II) and L represents a leaving group, for example a lower alkoxy or lower alkyl thio group with a hydrazine (IV)

in which $R_3$ is as defined in formula (I) and Z represents two hydrogen atoms. The reaction may be carried out in the presence of a suitable solvent such as an aromatic hydrocarbon, e.g. toluene, an alkanol, e.g. ethanol or isopropanol, water or dimethylformamide at a temperature of from room temperature to reflux. The compound of formula (II) is thus formed and cylises in situ to give the compound of the invention.

In a further embodiment of the process, compounds of formula (I) in which $R_4$ and $R_5$ are both hydrogen may also be prepared via the intermediate (II) from a diamine of formula (V)

in which $R_1$, $R_2$, Alk, Q, n, X and m are as defined in formula (II) by reaction with a compound of formula (VI)

in which $R_3$ is as defined in formula (I), L is as defined in formula (III) and Z represents two hydrogen atoms or a protecting group which can readily be removed to yield two hydrogen atoms, e.g. a benzylidene group.

The reaction may be carried out in the absence or presence of a suitable solvent, for example toluene, ethanol, methanol, isopropanol, acetonitrile or water, at a temperature from room temperature to reflux. When the reaction is carried out with a compound (VI) in which Z is a protecting group, it is necessary to remove the protecting group before cyclisation can take place. Where Z represents a benzylidene group it may be removed with aqueous acid, e.g. hydrochloric acid, and under these conditions the intermediate (II) where Z represents two hydrogen atoms cyclises to give the compound of formula (I). When Z represents a benzylidene group it may also be removed by heating with an amine e.g. piperidine, to give the compound of formula (I).

The compound of formula (VI) may be prepared from a compound of formula (VII)

in which L is as defined in formula (III) and L' may have one of the meanings of L or may represent a lower alkyl sulphoxide group. The compound (VII) is reacted with the hydrazine (IV) to give the compound of formula (VI) the reaction preferably being carried out in a solvent for example toluene, an alkanol or acetonitrile, and preferably with heating.

Compounds of formula (I) in which $R_4$ and $R_5$ are other than the group $=CR_8R_9$ may be prepared by cyclisation of a compound of formula (VIII)

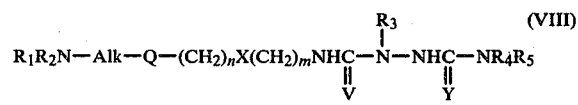

where V is NH and Y is sulphur, oxygen or NH or V is sulphur or oxygen and Y is NH, and in which $R_1$, $R_2$, Alk, Q, n, X, m, $R_3$, $R_4$ and $R_5$ are as defined in formula (I) except that $R_4$ and $R_5$ are other than the group $=CR_8R_9$. The reaction is preferably carried out by heating the compound (VIII) in a suitable solvent such as acetonitrile or dimethylformamide.

A compound (VIII) in which V is NH and Y is sulphur, oxygen or NH may be prepared by reacting an alkylisothiourea (IX)

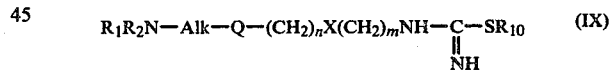

in which $R_{10}$ represents a $C_{1-4}$ alkyl group, with a semicarbazide thiosemicarbazide or aminoguanidine (X)

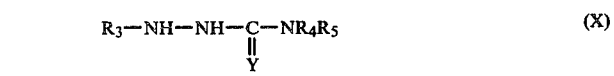

in which Y is oxygen, sulphur or NH, in a suitable solvent, e.g. dimethylformamide.

Compounds of formula (VIII) in which V is sulphur or oxygen Y is NH and $R_4$ and $R_5$ are both hydrogen or alkyl may be prepared by the reaction of the compound (XI)

in which Y is sulphur or oxygen and in which $R_1$, $R_2$, Alk, Q, n, X and m are as defined in formula (I), with an aminoguanidine (X) in which Y is NH and $R_3$ is as defined in formula (I) and $R_4$ and $R_5$ both represent hydrogen or alkyl. The reaction may be carried out preferably with heating, optionally in the presence of a suitable solvent such as a lower alkanol, e.g. ethanol, or acetonitrile.

Compounds of formula (I) in which $R_4$ and $R_5$ are other than hydrogen or the group $=CR_8R_9$ may be prepared from an aminoguanidine (XII)

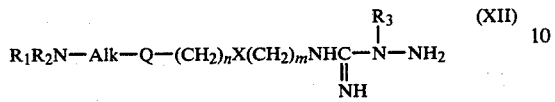

in which $R_1$, $R_2$, Alk, Q, n, X, m and $R_3$ are as defined in formula (I) by reaction with a carbamoyl halide (XIII)

in which $R_4$ and $R_5$ are as defined in formula (I) and are other than hydrogen or the group $=CR_8R_9$ and Hal is a halogen atom. The reaction is preferably carried out in a suitable solvent such as acetonitrile or an aromatic hydrocarbon, e.g. benzene or toluene.

The aminoguanidine (XII) may be prepared by the reaction of a thiourea (XIV)

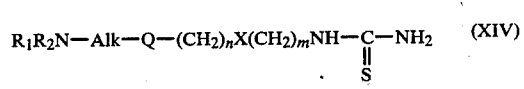

with an alkyl halide or a dialkyl sulphate in the presence of an acid to produce the alkylisothiourea (IX). Reaction of this alkylisothiourea (IX) with the hydrazine (IV) in a suitable solvent such as dimethylformamide, followed by removal of the protecting group Z where appropriate gives the aminoguanidine (XII).

Compounds of formula (I) in which $R_4$ and $R_5$ are other than the group $=CR_8R_9$ can be prepared by reducing a compound of formula (XV)

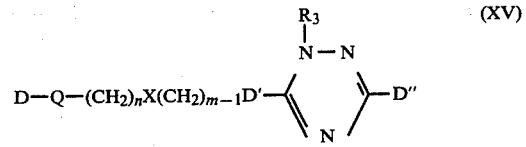

in which Q, n, X, m and $R_3$ are as defined in formula (I) and in which at least one of D, D' and D" represents a reducible group and the other(s) take the appropriate meaning corresponding to formula (I);

where D represents $R_1R_2NAlk$— or a group convertible thereto under the reducing conditions where $R_1$, $R_2$ and Alk are as defined in formula (I);

where D' represents —$CH_2NH$— or a group —$CONH$— or —$CH=N$—; and where D" represents $NR_4R_5$ where $R_4$ and $R_5$ are as defined in formula (I) or a group —$NR_4COR_{11}$ in which $R_4$ is as defined in formula (I) and $R_{11}$ represents hydrogen, alkyl, optionally substituted by a hydroxy group or a group convertible thereto under the reducing conditions aryl, aralkyl, or alkoxy.

Thus for example compounds of formula (I) in which $R_4$ and $R_5$ are other than the group $=CR_8R_9$ may be prepared by reducing compounds of formula (XVI)

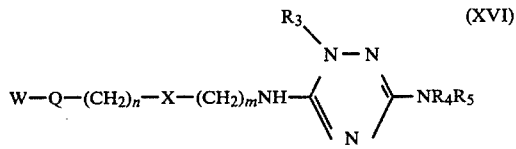

in which W represents the group —CHO or —$(CH_2)_p CONR_1R_2$, Q, n, X, m, $R_3$, $R_4$, $R_5$, $R_1$ and $R_2$ are as defined in formula (I) and p is zero, 1, 2, 3, 4 or 5. Compounds of formula (I) in which Alk represents $CH_2$ may be prepared from the compound (XVI) in which W represents the group —CHO by reaction with ammonia or an amine $R_1R_2NH$ in a solvent e.g. tetrahydrofuran or an alkanol such as ethanol or methanol, followed by reduction e.g. with a hydride reducing agent such as an alkali or alkaline earth metal borohydride, e.g. sodium borohydride, or aluminium hydride or lithium aluminium hydride or with hydrogen and a metal catalyst e.g. palladium or platinum.

Similarly compounds of formula (I) in which Alk is a $C_{1-6}$ alkylene group may be prepared by reduction of a compound of formula (XVI) in which W represents the group $R_1R_2NCO(CH_2)_p$. The reduction may be carried out with aluminium hydride or lithium aluminium hydride in a suitable solvent such as dioxan or tetrahydrofuran. The compounds of formula (XVI) may be prepared from an amine of formula (XVII)

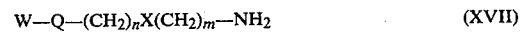

in which W represents the group $R_1R_2NCO(CH_2)_p$ or a protected aldehyde group e.g. an acetal or cyclic ketal, by methods analogous to those described herein for preparing the corresponding compounds of formula (I).

In a further aspect of the reduction of compounds of formula (XV) compounds of formula (I) in which $R_4$ and $R_5$ are other than the group $=CR_8R_9$ may be prepared by the reduction of an amide (XVIII)

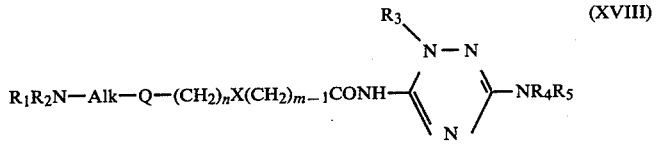

in which $R_1$, $R_2$, Alk, Q, n, X, m, $R_3$, $R_4$ and $R_5$ are as defined in formula (I), with a suitable reducing agent such as lithium aluminium hydride or an aluminium hydride in a solvent such as tetrahydrofuran or dioxan, at temperatures from ambient to reflux.

Compounds of formula (XVIII) in which $R_3$ is hydrogen and $R_4$ and $R_5$ are both hydrogen or alkyl or in which $R_3$ is other than hydrogen and $R_4$ and $R_5$ are both alkyl may be prepared from an activated derivative of a carboxylic acid (XIX)

and the appropriate diaminotriazole (XX)

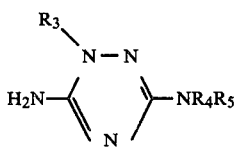 (XX)

in which $R_3$ is hydrogen and $R_4$ and $R_5$ are both hydrogen or alkyl or in which $R_3$ is other than hydrogen and $R_4$ and $R_5$ are both alkyl. Suitable activated acid derivatives include acyl halides, mixed acid anhydrides, esters, for example alkyl esters or (1-alkyl 2-pyridinyl) esters and products formed by reaction of the carboxylic acid with a coupling agent such as carbonyldiimidazole or a carbodiimide such as dicyclohexylcarbodiimide.

The intermediate diaminotriazole (XX) in which $R_4$ and $R_5$ are both other than hydrogen may be prepared by reaction of the carbamoyl halide (XIII) with the aminoguanidine (XXI)

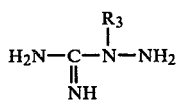 (XXI)

in a solvent such as benzene or acetonitrile.

In a further aspect of the reduction of compounds of formula (XV), compounds of formula (I) in which $R_4$ and $R_5$ are other than the group $=CR_8R_9$ may also be prepared by reduction of an imine (XXII)

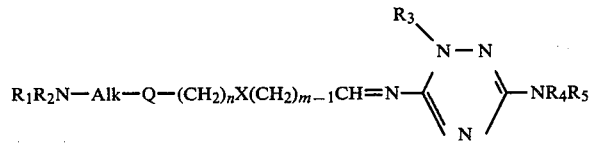 (XXII)

in which $R_1$, $R_2$, Alk, Q, n, X, m, $R_3$, $R_4$ and $R_5$ are as defined in formula (I). Suitable reducing agents include metal hydrides such as alkali or alkaline earth metal borohydrides, e.g. sodium borohydride, in a solvent such as an alkanol, e.g. methanol or ethanol, or aluminium hydride or lithium aluminium hydride in a solvent such as tetrahydrofuran or dioxan. The imine (XXII) may also be reduced with hydrogen and a suitable metal catalyst such as platinum, in a solvent such as an alkanol, e.g. methanol or ethanol.

The imine (XXII) may be formed by reaction of an aldehyde (XXIII)

$$R_1R_2N-Alk-Q-(CH_2)_nX(CH_2)_{m-1}CHO \quad (XXIII)$$

with the diaminotriazole (XX) in a suitable solvent such as benzene, toluene, ethanol or methanol, preferably with heating optionally in the presence of an acid catalyst, e.g. hydrochloric acid or p-toluene sulphonic acid.

In the above process it is sometimes unnecessary to isolate the imine (XXII). Thus, for example, treatment of a mixture of an aldehyde (XXIII) and a triazole (XX) in an appropriate solvent e.g. ethanol or methanol, with a suitable reducing agent, e.g. sodium borohydride, gives the compound of formula (I) directly.

In another aspect of the reduction process described above compounds, of formula (I) in which $R_4$ is —$CHR_8R_9$ and $R_5$ represents hydrogen can be prepared by the reduction of a compound of formula (XV) as defined above in which D" represents —$N=CR_8R_9$.

The reduction may conveniently be carried out with an alkali or alkaline earth metal borohydride such as sodium borohydride or with hydrogen and a metal catalyst such as platinum or palladium. Similarly compounds of formula (I) in which $R_4$ and $R_5$ are both alkenyl or alkyl optionally substituted by hydroxyl may be prepared by reacting a compound of formula (I) in which at least one of $R_4$ and $R_5$ are hydrogen with the appropriate aldehyde or ketone, followed by reduction by the procedure described above.

In a further embodiment of the reduction process described above compounds of formula (I) in which $R_1$ and/or $R_5$ are other than hydrogen may be prepared by reduction of a compound of formula (XV) in which D represents the group $R_1{}^aCONR_2Alk$ and/or the group D" represents the group —$NR_4COR_5{}^a$, where $R_1{}^a$ and $R_5{}^a$ have meanings such that under the conditions of the reduction the groups $R_1{}^aCO$ and $R_5{}^aCO$ are converted into the required groups $R_1$ and $R_5$.

The reduction is preferably carried out with aluminium hydride or lithium aluminium hydride in a solvent such as dioxan or tetrahydrofuran.

The compounds of formula (XV) in which D and/or D" have the meanings $R_1{}^aCONR_2Alk$ or —$NR_4COR_5{}^a$ may be prepared by treating a compound of formula (I) in which $R_1$ and/or $R_5$ represent hydrogen with an activated derivative of the appropriate acid $R_1{}^aCO_2H$ or $R_5{}^aCO_2H$.

Compounds of formula (I) can be produced by reacting a compound of the formula (XXIV)

$$R_1R_2NAlkQE \quad (XXIV)$$

in which E represents $(CH_2)_nX(CH_2)_mP$ or $CH_2P'$, where P and P' are leaving groups, with a compound of the formula (XXV).

 (XXV)

in which U represents hydrogen, $HS(CH_2)_m$ or $HO(CH_2)_m$

Thus for example compounds of formula (I) may be prepared by reacting a compound of formula (XXVI)

$$R_1R_2N-Alk-Q-(CH_2)_nX(CH_2)_mP \quad (XXVI)$$

in which $R_1$, $R_2$, Alk, Q, n, X and m are as defined in formula (I) and P represents a leaving group such as a mesyloxy or tosyloxy group, with the diaminotriazole (XXV) in which U represents hydrogen. The reaction is carried out in a suitable solvent such as dimethylformamide or acetonitrile.

Compounds of formula (XXVI) in which P represents a mesyloxy or tosyloxy group may be prepared from the corresponding alcohol (i.e. the compound of formula (XXVI) in which P represents a hydroxyl group) by reaction with the appropriate sulphonyl chloride. Compounds of formula (XXVI) in which P represents a hydroxyl group may for example be prepared by reduction of the corresponding acid (XIX) or an ester thereof.

As a further example of this reaction, compounds of formula (I) in which n is 1 and X is sulphur may be prepared by reacting a thiol (XXVII)

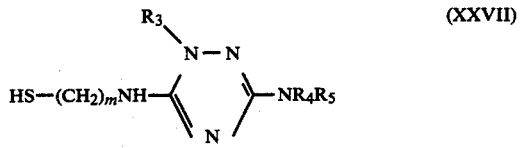

in which m, $R_3$, $R_4$ and $R_5$ are as defined in formula (I), with a compound (XXVIII)

$$R_1R_2N-Alk-Q-CH_2P' \qquad (XXVIII)$$

in which $R_1$, $R_2$, Alk and Q are as defined in formula (I) and P' represents a leaving group such as halogen a hydroxyl group or an acyloxy group, e.g. acetoxy.

When P' is other than a hydroxyl group the reaction is carried out in an organic solvent such as dimethylformamide in the presence of a strong base, e.g. sodium hydride. When P' is a hydroxyl the reaction is preferably carried out in the presence of a mineral acid such as hydrochloric acid and preferably at a temperature of 0° to 80° C.

Compounds of formula (I) in which n is 1 and X is oxygen may similarly be prepared by reacting the compound (XXVIII) in which P' is a hydroxyl group with an aminoalcohol (XXIX)

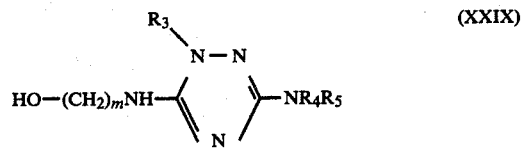

The reaction is carried out in a solvent such as tetrahydrofuran in the presence of a strong acid such as methane sulphonic acid or hydrochloric acid. In the above process the reaction with (XXVIII) in which P' is hydroxyl is preferably carried out when Q represents a furan or substituted furan group.

Compounds of formula (I) in which Q is other than benzene and Alk is methylene may be prepared by introducing a group $R_1R_2NCH_2$ into a compound of formula (XXX)

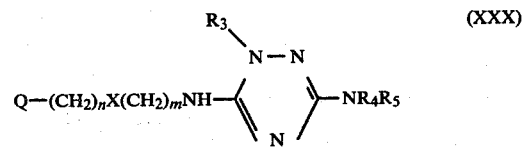

in which n, X, m, $R_3$, $R_4$ and $R_5$ are as defined in formula (I). Thus a compound of formula (I) in which Q is a furan or substituted furan ring may be prepared by reacting a compound of formula (XXX) with formaldehyde and an amine $R_1R_2NH$ or a salt thereof in which $R_1$ and $R_2$ are as defined in formula (I). The reaction may be carried out by reacting the amine salt with aqueous formaldehyde and the compound (XXX) or by refluxing the amine salt with paraformaldehyde and compound (XXX) in a solvent such as ethanol.

Compounds of formula (I) in which Q is other than benzene, Alk is $CH_2$ and $R_1$ and $R_2$ and methyl may be prepared by reacting compounds of formula (XXX) with the compound of formula (XXXI)

$$(CH_3)_2N^{\oplus}=CH_2Cl^{\ominus} \qquad (XXXI)$$

The reaction is carried out in a solvent such as acetonitrile at an elevated temperature e.g. reflux. The compounds of formula (XXX) may be prepared by methods analogous to those already described for the compounds of formula (I).

Compounds of formula (I) in which the groups $R_4$ and $R_5$ together represent the group $=CR_8R_9$ may be prepared from compounds of formula (I) in which $R_4$ and $R_5$ are both hydrogen by reaction with an aldehyde or ketone $R_8R_9CO$ in a solvent such as benzene, ethanol, or methanol. The reaction is preferably carried out with heating, e.g. at reflux.

Compounds of formula (I) in which $R_4$ and $R_5$ are both hydrogen can be converted into compounds of formula (I) in which $R_4$ and $R_5$ are both methyl by reaction with formic acid and formaldehyde using the Eschweiler-Clarke procedure.

Compounds of formula (I) can be prepared by reacting a compound of formula (XXXIII) or a compound of formula (XXXII; in which L" is a leaving group and can represent halogen e.g. bromine, acyloxy, e.g. acetoxy, or a quaternary ammonium group) with an amine $R_1R_2NH$ or $R_4R_5NH$ in which $R_1$, $R_2$, $R_4$ and $R_5$ are as defined in formula (I).

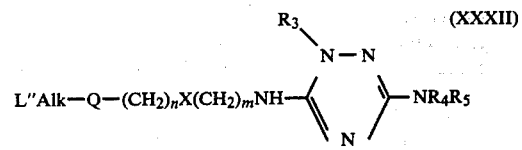

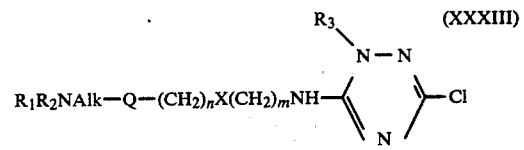

The reaction of the compounds (XXXII) in which Alk, Q, n, X, m, $R_3$, $R_4$ and $R_5$ are as defined in formula (I) and L" is halogen, with the amine $R_1R_2NH$ can be carried out in an inert solvent such as acetonitrile, in the presence of a base e.g. potassium carbonate. Displacement of the chlorine atom in the compound of formula (XXXIII) may be carried out by heating with the appropriate amine at elevated temperatures.

In a compound of formula (XXXII) where L" is a quaternary ammonium group the reaction with the amine $R_1R_2NH$ may be carried out in a suitable solvent such as acetonitrile or an alkanol, e.g. ethanol, at a temperature of ambient to reflux; this reaction is particularly useful for preparing compounds in which Alk is $CH_2$.

The compounds of formula (XXXII) may be prepared by conventional methods for example from the corresponding alcohol (compound of formula (XXXII) where L" is hydroxy) or the corresponding tertiary amino compound (compound of formula (I) where $R_1$ and $R_2$ are other than hydrogen).

The chloro-compound (XXXIII) can be prepared by treating the compound of formula (I) in which $R_4$ and $R_5$ are both hydrogen, with sodium nitrite in the presence of a mineral acid such as hydrochloric acid or sulphuric acid to give the diazonium salt (XXXIV)

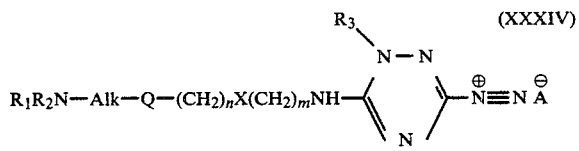

in which $A^\ominus$ is the anion of the acid used in the diazotisation. Reaction of the diazonium salt (XXXIV) with hydrochloric acid in the presence of an aqueous cuprous chloride solution, gives the required chloroderivative (XXXIII).

In some reactions in which a leaving group e.g. a quaternary ammonium group is displaced by an amine $R_1R_2NH$ in order to insert the group $R_1R_2N$ than cyclisation to form the triazole ring may occur. Thus compounds of formula (I) in which $R_4$ and $R_5$ are both hydrogen and Alk is $CH_2$ can be prepared by reacting a compound of formula (XXXV)

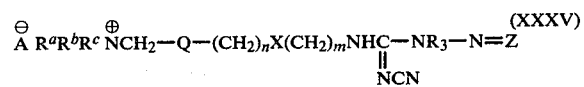

where $R^a$, $R^b$, and $R^c$ are alkyl or aralkyl, Q, n, X, m, and $R_3$ are as defined in formula (I) A is anion, e.g. halide and Z is a protecting group, e.g. benzylidene, with an amine of formula $R_1R_2NH$ in which $R_1$ and $R_2$ are as defined in formula (I) but are other than hydrogen. The compound of formula (XXXV) may be prepared by reacting a compound of formula (XXXVI)

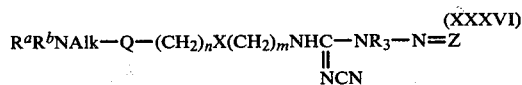

with an alkyl or aralkyl halide, e.g. methyl iodide or benzyl iodide.

In a process for the production of compounds of formula (I) where $R_1$ and $R_2$ are hydrogen a compound of formula (XXXII) where L" is a quaternary ammonium group e.g. trimethylammonium, Alk is $CH_2$ and Q, n, X, m, $R_3$, $R_4$ and $R_5$ are as defined in formula (I) is heated with a phthalimide salt e.g. potassium phthalimide, in a solvent e.g. dimethylformamide at an elevated temperature e.g. 150° C. to give the compounds of formula (XXXII) where L" is the group

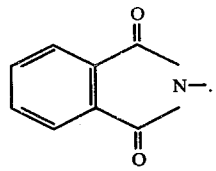

The phthalimide group is cleaned by standard procedures described earlier e.g. with hydrazine.

The compounds of formulae (III), (V) (XIV) (XI) (XVII) (XIX) and (XXVIII) may be prepared as described in German Offenlegungsschrifts Nos. 2,734,070, 2,821,400 and 2,821,409 or by methods analagous to those described in these documents. The aldehydes of formula (XXIII) can be made by partial reduction of acids of formula (XIX).

Where the product of any of the above processes is a free base and a salt is required, the salt may be formed in a conventional manner. Thus, for example, a generally convenient method of forming the salts is to mix appropriate quantities of the free base and the acid in an appropriate solvent(s), e.g. an alcohol such as ethanol or an ester such as ethyl acetate.

The invention is illustrated but not limited by the following Examples.

PREPARATION 1

N-Cyano-1-methyl-2-(phenylmethylene)hydrazinecarboximidothioic acid, methyl ester A mixture of cyanocarbonimidodithioic acid dimethyl ester (1.46 g) and benzaldehyde N-methyl hydrazone (1.34 g) in acetonitrile was heated under reflux for 50 hr. The reaction mixture was cooled to 25° to give the title compound as colourless crystals, m.p. 132°-133° (0.73 g).

T.l.c. silica gel, 0.25 mm thickness/ethyl acetate: light petroleum (b.p. 60°-80°) 1:4, single spot Rf 0.35.

Similarly prepared from benzaldehyde N-ethyl hydrazone (3 g) and cyanocarbonimidodithioic acid dimethyl ester (1.46 g) was N-cyano-1-ethyl-2-phenylmethylene)hydrazine carboximidothioic acid methyl ester (2.1 g) m.p. 138°-9°.

PREPARATION 2

3-[3-(1,3-Dioxolan-2-yl)phenoxy]propanamine

A solution of 2-[3-(3-formylphenoxy)propyl]-1H-isoindole-1,3-(2H)-dione (90 g) and p-toluenesulphonic acid, monohydrate (200 mg) in benzene (900 ml) and ethane-1,2-diol (25 g) was heated under reflux using a Dean-Stark separator for 8 h. The cooled solution was washed successively with sodium carbonate solution, water, sodium chloride solution, and evaporated in vacuo. The resulting oil was dissolved in tetrahydrofuran (1 liter) and stirred with hydrazine hydrate (50 ml) at room temperature for 24 hr. The mixture was diluted with ether and filtered. The filtrate was distilled to give the title compound as a colourless oil (55.2 g) b.p. 134°-6° (0.7 mm). TLC silica; methanol:ammonia 80:1; Rf 0.4.

N'-Cyano-N-[3-[3-(1,3-dioxolan-2-yl)phenoxy]-propyl]1-methyl-2-(phenylmethylene)hydrazinecarboximidamide 3-[3-(1,3-Dioxolan-2-yl)phenoxy]propanamine (8.92 g) and N-cyano-1-methyl-2-(phenylmethylene) hydrazinecarboximidothioic acid methyl ester (9.28 g) were heated under water-pump vacuum at 80° for 4 h to yield the title compound, a pale yellow glass (16.03 g). TLC silica; ethyl acetate:cyclohexane 1:1; Rf 0.2 NMR (CDCl$_3$) 2.3-2.2 m (10H); 4.36 s (1H), 5.8-6.1 m (8H); 6.55 s (3H); 7.83 m (2H).

PREPARATION 3

3-(1-Piperidinylmethyl)benzoic acid, methyl ester

A mixture of piperidine (25 ml) and 3-(bromomethyl) benzoic acid, methyl ester (20 g) in toluene (600 ml) was stirred at room temperature for 4 h. The white precipitate was removed by filtration and the filtrate was distilled to give the title compound as a colourless oil (17.56 g) b.p. 110° ($10^{-1}$ mm). TLC silica; ether; Rf 0.7.

3-(1-Piperidinylmethyl)benzenemethanol

A mixture of 3-(1-piperidinylmethyl)benzoic acid, methyl ester (17.56 g) and lithium aluminium hydride (2.68 g) in tetrahydrofuran (500 ml) was stirred at room temperature for 30 h and quenched with water. The solid was removed by filtration and the filtrate distilled to give the title compound as a colourless oil (11.1 g) b.p. 135° ($10^{-1}$ mm). TLC silica; ether; Rf 0.2.

2-[[[3-(1-Piperidinylmethyl)phenyl]methyl]thio]ethanamine

A mixture of 3-(1-piperidinylmethyl)benzenemethanol (10.8 g) and cysteamine hydrochloride (6.48 g) in concentrated hydrochloric acid (25 ml) was heated at 100° for 3 h. The cooled mixture was added to ether (500 ml) and treated with an excess of sodium carbonate. The organic solution was filtered and distilled to give the title compound as an oil (9.51 g) b.p. 175° ($6 \times 10^{-2}$ mm). TLC silica; ethyl acetate:water:isopropanol:0.88 amonia 25:8:15:2; Rf 0.7.

PREPARATION 4

2-[3-[4-[2-(Dimethylamino)ethyl]phenoxy]propyl]-1H-isoindole-1,3-(2H)-dione

A mixture of 4-[2-(dimethylamino)ethyl]phenol (4.13 g) and sodium hydride (0.67 g) in dimethylformamide was stirred at room temperature for 24 h. N-(3-Bromopropyl) phthalimide (6.7 g) was added at 0° and stirring was continued for 24 h. The solution was treated with water and extracted with ether. Evaporation of the solvent gave the title compound as a white solid which was recrystallised from light petroleum (b.p. 60°–80°) 2.3 g) m.p. 81°–82°. TLC silica; ethyl acetate:water:isopropanol:0.88 ammonia 25:8:15:2; Rf 0.45.

Similarly prepared from 4-[3-(dimethylamino)propyl]phenol (7.2 g) sodium hydride (1.06 g) and N-(3-bromopropyl)phthalimide (10.7 g) was 2-[3-[4-[3-(dimethylamino)propyl]phenoxy]propyl]-1H-isoindole-1,3-(2H)-dione (5.2 g) m.p. 67°–67.5°. TLC Silica, ethyl acetate/water/isopropanol/0.88 ammonia 25:8:15:2, Rf 0.5.

4-[3-Aminopropoxy]-N,N-dimethylbenzeneethanamine

2-[3-[4-[2-(Dimethylamino)ethyl]phenoxy]propyl]-1H-isoindole-1,3-(2H)-dione (2.1 g) and hydrazine hydrate (1.2 ml) were heated at reflux in ethanol for 4 h. The solvent was evaporated and the residue was distilled to give the title compound as a clear yellow oil b.p. 170° (0.1 mm). TLC silica; ethyl acetate:water:isopropanol:0.88 ammonia 25:8:15:2; Rf 0.35.

Similarly prepared from 2-[3-[4-[3-(dimethylamino)propyl]phenoxy]propyl]-1H-isoindole-1,3-(2H)-dione (4.4 g) and hydrazine hydrate (3 ml) was 4-(3-aminopropoxy)-N,N-dimethylbenzenepropanamine (2 g) b.p. 150°/0.06 mm. TLC silica, ethyl acetate/water/isopropanol/0.88 ammonia 25:8:15:2, Rf 0.2.

PREPARATION 5

3-[3-[1-Piperidinylmethyl]phenoxy]propanamine

2-[3-[3-Formylphenoxy]propyl]-1H-isoindole-1,3-dione (50 g) and piperidine (20.7 g) in ethyl acetate (750 ml) were hydrogenated over 10% palladium/carbon catalyst. The catalyst was removed by filtration and the solvent evaporated and hydrazine hydrate (40 ml) was added to an ethanolic solution of the residue at 25°. After 67 hr the reaction mixture was diluted with ether, filtered and the filtrate was distilled to give the title compound as a colourless oil (31.05 g) b.p. 154°–8°/0.15 mm. TLC silica, methanol/0.88 ammonia 80:1, Rf 0.2.

The following compounds were similarly prepared from the appropriate phthalimide (A) and the corresponding amine.

(ii) A (50 g) and hexamethyleneimine (25 g) gave 3-[3-[1-hexamethyleneiminylmethyl]phenoxy]propanamine (19.4 g) b.p. 170°–4°/0.25 mm. TLC silica, methanol/0.88 ammonia 80:1, Rf 0.2.

(iii) A (5 g) and 2,2,2-trifluoroethylamine (3.21 g) gave 3-[3-aminopropoxy]-N-(2,2,2-trifluoroethyl) benzenemethanamine (1.5 g) b.p. 130°/0.1 mm. TLC silica, ethyl acetate/water/isopropanol/0.88 ammonia 25:8:15:2, Rf 0.57.

(iv) A (25 g) and N-methylbutylamine (20 ml) gave 3-[3-aminopropoxy]-N-butyl-N-methylbenzenemethanamine (1.84 g) b.p. 135°/0.1 mm. TLC silica, ethyl acetate/water/isopropanol/0.88 ammonia 25:8:15:2, Rf 0.36.

(v) A (15.5 g) and piperidine (15 ml) gave 3-[4-(1-piperidinylmethyl)phenoxy]propanamine (4.92 g) b.p. 200°/0.1 mm. TLC silica, methanol/0.88 ammonia 80:1, Rf 0.2.

PREPARATION 6

3-(1-Piperidinylmethyl)phenol

3-Hydroxybenzaldehyde (15 g) and piperidine (15 ml) in ethanol (500 ml) were hydrogenated over 10% palladium/carbon catalyst. The catalyst was removed by filtration and the solvent was evaporated off. The residue was triturated with light petroleum (b.p. 60°–80°) and the resulting solid was recrystallised from acetonitrile to give the title compound as a buff coloured solid (8.7 g) m.p. 134°–7°. TLC silica, methanol, Rf 0.56.

4-[3-(1-Piperidinylmethyl)phenoxy]butanamine

A mixture of 3-(1-piperidinylmethyl)phenol (8.7 g) and sodium hydride (1.2 g) in dimethylformamide (60 ml) was stirred at 25° during 3 h. N-(4-Bromobutyl) phthalimide (12.8 g) was added and the mixture was stirred at 25° during 20 h then at 65° for 3 h. The reaction mixture was poured onto water and extracted with ethyl acetate. The solvent was concentrated and the crystalline impurity was removed by filtration. The filtrate was evaporated in vacuo and the residue was dissolved in ethanol and heated at reflux with hydrazine hydrate (2.5 ml) for 3 h. The mixture was filtered and the filtrate distilled to give the title compound as a colourless oil (4.1 g) b.p. 140°/0.1 mm TLC silica, ethyl acetate/water/isopropanol/0.88 ammonia 25:8:15:2, Rf 0.32.

PREPARATION 7

5-[(4-Aminobutoxy)methyl]-N,N-dimethyl-2-furanmethanamine

A mixture of methanesulphonic acid (86 g), 5-[(dimethylamino)methyl]-2-furanmethanol (15.5 g) and 4-aminobutanol (17.8 g) in dry tetrahydrofuran was heated at 100° for 1½ h. Excess sodium carbonate was added to the cooled solution, the suspension was filtered and the filtrate was evaporated to give a red oil which was dissolved in water and extracted with ether. The extract was distilled to give the title compound as an oil (6.6 g) b.p. 100°–110°, 0.08 mm. TLC silica, methanol/ammonia 0.88 80:1, Rf 0.3.

PREPARATION 8

2-[3-[4-Formylphenoxy]propyl]-1H-isoindole-1,3-dione

4-Hydroxybenzaldehyde (24.4 g) and sodium hydride (4.8 g) in dry dimethylformamide (400 ml) were stirred at room temperature for 3 h. N-(3-Bromopropyl)phthalimide (55.0 g) was added and the reaction was stirred for a further 5 h. The mixture was poured onto ice and the resulting white solid was recrystallized from a mixture of dichloromethane and cyclohexane to yield the title compound (42.2 g) m.p. 120°–1°. TLC silica, ethyl acetate, Rf 0.7.

PREPARATION 9

3-[3-[[[(Cyanimino)[1-methyl-2-(phenylmethylene)hydrazino]]methyl]amino]propoxy]-N,N,N-trimethylbenzenemethanium iodide 3-(3-Aminopropoxy)-N,N-dimethylbenzenemethanamine (2.2 g) and N-cyano-1-methyl-2-(phenylmethylene) hydrazine carboximidothoic acid methyl ester (2.52 g) were heated together at 100° for 2 h to give a red oil which was dissolved in acetone and treated with methyl iodide (1.7 g) at room temperature. After 2 h solvent was removed to give the title compound as a white solid which was washed with ether (5.58 g). TLC alumina, aqueous ammonia (1.4%) Rf 0.45 NMR (DMSO $d_6$) 1.7 t (1H); 1.9 s (1H); 1.9–2.2 s (2H); 2.5–2.65 m (4H); 2.7–2.9 m (3H); 5.37 s (2H); 5.8 t (2H); 6.15 q (2H); 6.45 s (3H); 6.83 s (9H); 7.80 m (2H).

PREPARATION 10

3-[3-[[3-Amino-1-methyl-1H-1,2,4-triazol-5-yl]amino]propoxy]-N,N,N-trimethylbenzenemethanium iodide Methyl iodide (1.9 g) and 1-methyl-$N^5$-[3-[3-[(dimethylamino)methyl]phenoxy]propyl]-1H-1,2,4-triazole-3,5-diamine (3.9 g) in acetonitrile were stirred at room temperature for 45 min. The suspension was heated at 100° for 15 min to give the title compound as a yellow solid which was collected and washed with acetonitrile (4.6 g) m.p. 178°–179°.

PREPARATION 11

Following the method of Preparation 5:
(i) A (10 g) and 4-hydroxypiperidine (6.54 g) gave 3-[3-[1-(4-hydroxypiperidinyl)methyl]phenoxy]-propanamine (3.6 g) b.p. 180°/0.1 mm. TLC silica, ethyl acetate/water/isopropanol/0.88 ammonia 25:8:15:2, Rf 0.2.
(ii) A (16.34 g) and diethylamine (15 ml) gave 3-[3-aminopropoxy]-N,N-diethylbenzene methanamine (2.63 g) b.p. 130°/0.1 mm. TLC silica, ethyl acetate/water/isopropanol/0.88 ammonia 25:8:15:2, Rf. 0.4.

PREPARATION 12

1-Methyl-$N^5$-(3-hydroxypropyl)-1H-1,2,4-triazole-3,5-diamine

N'-Cyano-N-[1-(3-hydroxypropyl)]-N''-[(phenylmethylene)amino]-N''-methyl-guanidine A solution of 3-aminopropyl (3 g) and N-cyano-1-methyl-2-(phenylmethylene)hydrazine carboximidothioic acid, methyl ester (9.8 g) in acetone (50 ml) was heated under reflux for 6 h. The reaction was cooled and the precipitate that formed was filtered off and recrystallised from ethyl acetate to give the title compound as a white solid (3.9 g) m.p. 126°–7°. TLC silica, ethyl acetate, Rf 0.35.

1-Methyl-$N^5$-(3-hydroxypropyl)-1H-1,2,4-triazole-3,5-diamine

A solution of N'-cyano-N-[1-(3-hydroxypropyl)]-N''-[(phenylmethylene)amino]-N''-methyl-guanidine (3.9 g) and 2 N hydrochloric acid (20 ml) in acetone (100 ml) was stirred at 25° for 18 h. Sodium carbonate was added and the solvent removed in vacuo. The residue was crystallised from acetonitrile to give the title compound as a white solid (2.2 g) m.p. 139°–140°. TLC silica, ethyl acetate/isopropanol/water/0.88 ammonia 25:8:15:2, Rf 0.5.

EXAMPLE 1

1-Methyl-$N^5$-[3-[3-[(dimethylamino)methyl]phenoxy]-propyl]-1H-1,2,4-triazole-3,5-diamine N'-Cyano-N-[3-[3-[(dimethylamino)methyl]phenoxy]-propyl]carbamimidothioic acid, methyl ester A mixture of 3-(3-aminopropoxy)-N,N-dimethylbenzenemethanamine (5 g) and cyanocarbonimidodithioic acid, dimethyl ester (3.5 g) in ether was stirred at 25° for 3 hours. The product (6.7 g) was filtered off and washed with ether, m.p. 118°–9°.

Similarly prepared from 3-[3-(1-piperidinylmethyl)-phenoxy]propanamine] (10 g) and cyanocarbonimidodithioic acid, dimethyl ester (5.84 g) was N'-cyano-N-[3-[3-(1-piperidinylmethyl)phenoxy]propyl]-carbamimidothioic acid methyl ester (11.5 g) m.p. 89°–90°.

1-Methyl-$N^5$-[3-[3-[(dimethylamino)methyl]phenoxy]-propyl]-1H-1,2,4-triazole-3,5-diamine N-Cyano-N-[3-[3-[(dimethylamino)methyl]phenoxy]-propyl]-carbamimidothioic acid methyl ester (1.5 g) and N-methylhydrazine (1.2 g) in dimethylformamide (15 ml) were heated at 40° for 24 hours. The solvent was removed, and the residue was triturated with ether to yield the title compound as a white solid (1.0 g) m.p. 95°–96.5°.

T.l.c. silica gel, 0.25 mm thickness, methanol:0.880 ammonia 80:1, single spot Rf 0.4.

EXAMPLE 2

1-Methyl-$N^5$-[3-[3-[(dimethylamino)methyl]phenoxy]-propyl]-1H-1,2,4-triazole-3,5-diamine A mixture of N-cyano-1-methyl-2-(phenylmethylene)hydrazine-carboximidothioic acid methyl ester (166 mg) and 3-(3-aminopropoxy)-N,N-dimethylbenzenemethanamine (104 mg) was heated at 45° under a reduced pressure of 20 mm of mercury for 3 hr. Acetone was added, and the resulting solution treated with dilute hydrochloric acid for 1 hour at room temperature. The mixture was diluted with water, washed with ether, basified with excess sodium carbonate and extracted with ethyl acetate. Evaporation of the ethyl acetate extracts gave an oil which crystallised from ethyl acetate/light petroleum b.p. 60°–80° to give the title compound as colourless crystals m.p. 95°–96.5° (87 mg).

T.l.c. silica gel, 0.25 mm thickness, methanol:0.88 ammonia 80:1, single spot Rf 0.4.

The following compounds were similarly prepared from the appropriate diamine and the corresponding N-cyano-1-alkyl-2-(phenylmethylene)hydrazine carboximidothioic acid methyl ester (A).

(ii) Diamine (1 g) and A (1.05 g) gave 1-methyl-$N^5$-[3-[4-[2-(dimethylamino)ethyl]phenoxy]propyl]-1H-1,2,4-triazole-3,5-diamine (0.47 g) m.p. 125°–126°. TLC silica, ethyl acetate/water/isopropanol/0.88 ammonia 25:8:15:2, Rf 0.56.

(ii) Diamine (0.5 g) and A (0.5 g) gave 1-ethyl-$N^5$-[3-[3-(1-piperidinylmethyl)phenoxy]propyl]-1H-1,2,4-triazole-3,5-diamine (0.48 g) m.p. 116.5°–118°. TLC silica, ethyl acetate/water/isopropanol/0.88 ammonia 25:8:15:2, Rf 0.6.

EXAMPLE 3

1-Methyl-$N^5$-[3-[3-[(dimethylamino)methyl]phenoxy]propyl]-1H-1,2,4-triazole-3,5-diamine N-Cyano-1-methylhydrazinecarboximidothioic acid, methyl ester A mixture of methyl hydrazine (0.48 ml) and cyanocarbonimidodithioic acid dimethyl ester (1.3 g) in acetonitrile was stirred at 25° for 16 hours. The resulting solution was evaporated to a gum which was crystallized from acetonitrile/ether to give the title compound as colourless granules (210 mg) m.p. 69°–71°.

T.l.c. silica gel 0.25 mm thickness, methanol; single spot Rf 0.7.

1-Methyl-$N^5$-[3-[3-[(dimethylamino)methyl]phenoxy]propyl]-1H-1,2,4-triazole-3,5-diamine A mixture of N-cyano-1-methylhydrazinecarboximidothioic acid methyl ester (200 mg) and 3-(3-aminopropoxy)-N,N-dimethylbenzenemethanamine (289 mg) was heated at 40° under a reduced pressure of 20 mm of mercury for 4 hours. The reaction mixture was cooled, triturated with ether and the resulting solid recrystallised from ethyl acetate to give the title compound as colourless crystals (246 mg) m.p. 95°–96.5°.

T.l.c. silica gel 0.25 mm thickness, methanol:0.880 ammonia 80:1, single spot Rf 0.4.

EXAMPLE 4

1-Methyl-$N^5$-[2-[[[5-(dimethylamino)methyl-2-furanyl]methyl]thio]ethyl]-1H-1,2,4-triazole-3,5-diamine oxalate N'-Cyano-N-[2-[[[5-(dimethylamino)methyl-2-furanyl]methyl]thio]ethyl]-N''-[(phenylmethylene)amino]-N''-methylguanidine A mixture of N-cyano-1-methyl-2-(phenylmethylene)hydrazine carboximidothioic acid methyl ester (4.64 g) and 2-[[[5-(dimethylamino)methyl-2-furanyl]methyl]thio]ethanamine (4.28 g) was heated at 40° under a reduced pressure of 20 mm of mercury for 3 hr. The resulting solid was crystallised from ethyl acetate/light petroleum (b.p. 60°–80°) to give the title compound (7.96 g) as white fibrous crystals, m.p. 94°–97°. TLC silica gel, 0.25 mm thickness, methanol:0.88 ammonia 80:1, single spot Rf 0.7.

1-Methyl-$N^5$-[2-[[[5-(dimethylamino)methyl-2-furanyl]methyl]thio]ethyl]-1H-1,2,4-triazole-3,5-diamine, oxalate A solution of N'-cyano-N-[2-[[[5-(dimethylamino)methyl-2-furanyl]methyl]thio]ethyl]-N''-[(phenylmethylene)amino]-N''-methyl-guanidine (3.98 g) in acetone was treated with dilute hydrochloric acid for 1 hour at room temperature. The resulting mixture was diluted with water, evaporated free of acetone, and washed with ether. The aqueous mixture was basified with excess sodium carbonate and extracted with ethyl acetate. Evaporation of the ethyl acetate extracts gave a gum which was dissolved in ethanol and treated with an excess of a solution of oxalic acid in ethanol to give the title compound (3.69 g) as small white prisms m.p. 163°–164° (dec.). TLC silica gel, 0.25 mm thickness, methanol:0.88 ammonia 80:1, single spot Rf 0.4.

EXAMPLE 5

$N^5$-[2-[[[5-(Dimethylamino)methyl-2-furanyl]methyl]thio]ethyl]-1H-1,2,4-triazole-3,5-diamine N-Cyano-N'-[2-[[[5-(dimethylamino)methyl-2-furanyl]methyl]thio]ethyl]carbamimidothioic cid, methyl ester 2-[[[5-(Dimethylamino)methyl-2-furanyl]methyl]thio]ethanamine (1.07 g) was added to a solution of cyanocarbonimidodithioic acid, dimethyl ester (0.73 g) in ether, and stirred overnight. The crystalline solid which formed was filtered off, washed with ether and dried to give N-cyano-N'-[2-[[[5-(dimethylamino)-methyl-2-furanyl]methyl]thio]ethyl]carbamimidothioic acid, methyl ester (1.14 g) m.p. 78°–79°.

$N^5$-[2-[[[5-(Dimethylamino)methyl-2-furanyl]methyl]thio]ethyl]-1H-1,2,4-triazole-3,5-diamine Hydrazine hydrate (3.5 ml) was added to a solution of N-cyano-N'-[2-[[[5-(dimethylamino)methyl-2-furanyl]methyl]thio]ethyl]carbamimidothioic acid, methyl ester (5.47 g) in ethanol (40 ml). After stirring for 3 days at room temperature the solvent was removed and the residual oil crystallised from water to give the title compound as white needles (2.95 g) m.p. 76°–78.5°.

EXAMPLE 6

(i)

$N^5$-[3-[3-[(Dimethylamino)methyl]phenoxy]propyl]-1H-1,2,4-triazole-3,5-diamine N'-Cyano-N-[3-[3-[(dimethylamino)methyl]phenoxy]propyl]-carbamimidothioic acid, methyl ester (1.0 g) and hydrazine hydrate (825 mg) were stirred at 25° for 3 days in ethanol. The solvent was removed and the residue crystallised from water to give a white solid (870 mg) m.p. 92°–3°.

(ii) Similarly prepared from N'-cyano-N-[3-[3-(1-piperidinylmethyl)phenoxy]propyl]-carbamimidothioic acid, methyl ester (14.1 g) and hydrazine hydrate (10 ml) was $N^3$-[3-[3-(1-piperidinylmethyl)phenoxy]propyl]-1H-1,2,4-triazole-3,5-diamine (10.4 g) m.p. 100°–101.5°. TLC silica; ethyl acetate:water:isopropanol:0.88 ammonia 25:8:15:2; Rf 0.4.

EXAMPLE 7

1-Methyl-$N^5$-[3-[3-[1-pyrrolidinylmethyl]phenoxy]propyl]-1H-1,2,4-triazole-3,5-diamine A mixture of 3-[3-[1-pyrrolidinylmethyl]phenoxy]propanamine (0.97 g) and N-cyano-1-methyl-2-(phenylmethylene)hydrazine carboximidothioic acid methyl ester (0.97 g) was heated at 70° for 8 hr under a reduced pressure of 20 mm of mercury. Acetone was added and the solution was treated with hydrochloric acid at room temperature for one hour, washed with ether, basified with sodium carbonate and extracted with ethyl acetate. Evaporation of the ethyl acetate extracts gave a thick oil which crystallised from ethyl acetate/light petroleum (b.p. 60–80″) to give the title compound as a white solid (0.2 g). TLC; silica/methanol/0.88 ammonia 80:1) Rf 0.5, m.p. 95°–95.5°.

The following compounds were similarly prepared from the corresponding diamine and the corresponding N-cyano-1-alkyl-2-(phenylmethylene)hydrazine carboximidothioic acid methyl ester (A).

(ii) Diamine (1.7 g) and A (2 g) gave $N^5$-[3-[3-[(dimethylamino)methyl]phenoxy]propyl]-1-ethyl-1H-1,2,4-triazole-3,5-diamine (0.22 g) m.p. 104°–105°. TLC Silica, methanol:0.88 ammonia 80:1, Rf 0.53.

(iii) Diamine (0.25 g) and A (0.23 g) gave 1-methyl-$N^5$-[2-[[[5-[1-pyrrolidinylmethyl]-2-thienyl]methyl]thio]ethyl]-1H-1,2,4-triazole-3,5-diamine (0.13 g), m.p. 99.5°–104.5°. TLC silica, ethyl acetate/water/isopropanol/0.88 ammonia 25:8:15:2, Rf 0.6.

(iv) Diamine (4.9 g) and A (4.33 g) gave 1-methyl-$N^5$-[3-[3-[1-hexamethylene iminylmethyl]phenoxy]propyl]-1H-1,2,4-triazole-3,5-diamine (6.82 g) m.p. 106°–7°. TLC silica, methanol/0.88 ammonia 80:1, Rf 0.5.

(v) Diamine (0.42 g) and A (0.46 g) gave 1-methyl-$N^5$-[4-[2-(dimethylamino)methyl-5-thienyl]butyl]-1H-1,2,4-triazole-3,5-diamine (0.18 g) b.p. 190° (0.05 mm). TLC silica; ethyl acetate:water:isopropanol:0.88 ammonia 25:8:15:2; Rf 0.5.

(vi) Diamine (0.8 g) and A (0.8 g) gave 1-methyl-$N^5$-[2-[[[5-(dimethylamino)methyl-4-methyl-2-furanyl]methyl]thio]ethyl]-1H-1,2,4-triazole-3,5-diamine (0.65 g). TLC silica; methanol:0.88 ammonia 79:1; Rf 0.4 NMR (CDCl$_3$) 4.01 s (1H); 5.40 t (1H); 5.06 brs (2H); 6.32 s (2H); 6.56 q; 6.60 s and 6.65 s (7H); 7.20 m (2H); 7.76 s (6H); 8.02 s (3H).

(vii) Diamine (1.54 g) and A (1.16 g) gave 1-methyl-$N^5$-[[[5-(dimethylamino)methyl-2-furanyl]methoxy]propyl]-1H-1,2,4-triazole-3,5-diamine (0.52 g). TLC silica; methanol:0.88 ammonia 79:1; Rf 0.5. NMR (CDCl$_3$) 3.75 d (1H); 3.86 d (1H); 5.20 t (1H); 5.58 s (2H); 6.00 brs (2H); 6.40 t (2H); 6.60 s; 6.62 q and 6.73 s (7H); 7.76 s (6H); 8.12 m (2H).

(viii) Diamine (0.9 g) and A (0.8 g) gave 1-methyl-$N^5$-[2-[[[5-(dimethylamino)methyl-4-(1-methyl)ethyl-2-furanyl]methyl]thio]ethyl]-1H-1,2,4-triazole-3,5-diamine (0.54 g) m.p. 76°–8°. TLC silica; methanol; 0.88 ammonia 79:1; Rf 0.3.

(ix) Diamine (3 g) and A (2.63 g) gave 1-methyl-$N^5$-[2-[[[3-(1-piperidinylmethyl)phenyl]methyl]thio]ethyl]-1H-1,2,4-triazole-3,5-diamine (0.78 g) m.p. 92°–93°. TLC silica; ethyl acetate:water:isopropanol:0.88 ammonia 25:8:15:2; Rf 0.7.

(x) 2-[[[2-[1-Piperidinylmethyl]-5-furanyl]methyl]thio]ethanamine (2.54 g) and A (2.32 g) gave 1-methyl-$N^5$-[2-[[[2-[1-piperidinylmethyl]-5-furanyl]methyl]thio]ethyl]-1H-1,2,4-triazole-3,5-diamine (3.1 g) b.p. 250° (0.08 mm). TLC silica; ethyl acetate:water:isopropanol:0.88 ammonia 25:8:15:2; Rf 0.6.

(xi) Diamine (0.47 g) and A (0.46 g) gave 1-methyl-$N^5$-[3-[4-[3-(dimethylamino)propyl]phenoxy]propyl]-1H-1,2,4-triazole-3,5-diamine (0.36 g) m.p. 111.5°–113.5°. TLC silica, ethyl acetate/water/isopropanol/0.88 ammonia 25:8:15:2, Rf 0.3.

(xii) Diamine (2.3 g) and A (2.04 g) gave 1-methyl-$N^5$-[3-[3-[(2,2,2-trifluoroethylamino)methyl]phenoxy]propyl]-1H-1,2,4-triazole-3,5-diamine (1.58 g) m.p. 62°–64°. TLC silica, ethyl acetate/water/isopropanol/0.88 ammonia 25:8:15:2, Rf 0.55.

(xiii) Diamine (1.8 g) and A (1.67 g) gave 1-methyl-$N^5$-[3-[3-[(butylmethylamino)methyl]phenoxy]propyl]-1H-1,2,4-triazole-3,5-diamine (1.25 g). TLC silica, ethyl acetate/water/isopropanol/0.88 ammonia 25:8:15:2; Rf 0.47. NMR (CDCl$_3$) 2.77 t, 1H; 3.0–3.33, m, 3H; 5.52 t (1H); 5.6–6.2 brs, (2H); 5.9, t (2H); 6.47 q (2H); 6.52 s (3H); 6.61, s (2H); 7.63 m (2H); 7.83 s (3H); 7.93 m (2H); 8.3–8.9, m (4H); 9.10, m (3H).

(xiv) Diamine (2.0 g) and A (1.8 g) gave 1-methyl-$N^5$-[4-[3-(1-piperidinylmethyl)phenoxy]butyl]-1H-1,2,4-triazole-3,5-diamine (0.67 g) m.p. 82°–82.5°. TLC silica; ethyl acetate/water/isopropanol/0.88 ammonia 25:8:15:2, Rf 0.42.

(xv) Diamine (0.46 g) and A (0.37 g) gave 1-methyl-$N^5$-[2-[[4-bromo-5-(dimethylamino)methyl-2-furanylmethyl]thio]ethyl]-1H-1,2,4-triazole-3,5-diamine (0.6 g) NMR (CDCl$_3$) 3.75 s (1H); 5.6 t (1H); 6.15 brs (2H); 6.3 s (2H); 6.53 s (2H); 6.6 s (3H); ca. 6.6 t (2H); 7.2 t (2H); 7.73 s (6H); IR (CHBr$_3$) 3480, 3380, 3430, 1548, 1010, 840 cm$^{-1}$.

(xvi) Diamine (0.5 g) and A (0.46 g) gave 1-methyl-$N^5$-[2-[[4-methoxymethyl-5-[(dimethylamino)methyl]-2-furanylmethyl]thio]ethyl]-1H-1,2,4-triazole-3,5-diamine (0.45 g). NMR (CDCl$_3$) 3.78 s (1H); 5.73 s (2H); 5.55 t (1H); 6.15 brs (2H); 6.15 s (2H); 6.4–6.7 3s t (10H); 7.22 t (2H); 7.77 s (6H); IR (CHBr$_3$) 3460, 3380, 2770, 2815, 1582, 1548, 1075, 840 cm$^{-1}$.

(xvii) Diamine (1.8 g) and A (1.74 g) gave 1-methyl-$N^5$-[2-[[5-[(dimethylamino)methyl]-2-furanyl]methoxy]ethyl]-1H-1,2,4-triazole-3,5-diamine (1.55 g) m.p. (oxalate salt) 131°–133°. TLC silica, methanol/0.88 ammonia Rf 0.5.

(xviii) Diamine (1.24 g) and A (1.16 g) gave 1-methyl-$N^5$-[3-[4-(1-piperidinylmethyl)phenoxy]propyl]-1H-1,2,4-triazole-3,5-diamine (1.26 g) m.p. 104°–105°. TLC silica, methanol/0.88 ammonia 80:1, Rf 0.5.

EXAMPLE 8

1-Methyl-$N^5$-[3-[3-[1-pyrrolidinylmethyl]phenoxy]propyl]-1H-1,2,4-triazole-3,5-diamine N'-Cyano-N-[3-[3-(1-pyrrolidinylmethyl)phenoxy]propyl]carbamimidothioic acid, methyl ester A solution of N-cyano-carbonimidodithioic acid dimethyl ester (5 g) in ethyl acetate (50 ml) was added to a solution of 3-[3-(1-pyrrolidinylmethyl)phenoxy]propanamine in ethyl acetate (60 ml). The reaction mixture was stirred at room temperature for 1 hr to give the title compund as an off-white solid m.p. 107°–108.5° (7.45 g). TLC silica; ethyl acetate:isopropanol:water:0.88 ammonia (25:15:8:2) single spot Rf 0.7.

1-Methyl-$N^5$-[3-[3-(1-pyrrolidinylmethyl)phenoxy]propyl-1H-1,2,4-triazole-3,5-diamine Methyl hydrazine (6.9 g) and dry dimethylformamide (10.95 g) were heated at reflux in toluene for 1 hr. N'-Cyano-N-[3-[3-(1-pyrrolidinylmethyl)phenoxy]propyl]-carbamimidothioic acid, methyl ester (10 g) was then added and the mixture heated at reflux for 5 hr. Evaporation of the solvent gave the title compound as a yellow oil which was converted to the fumarate salt in ethanol. The title compound was regenerated as the free base with aqueous sodium carbonate, and extracted into ethyl acetate. Evaporation of the solvent and trituration of the residue with light petroleum (b.p. 60°–80°) gave the title compound as a white solid (3.4 g) m.p. 95°–95.5°. TLC silica; methanol:0.88 ammonia (80:1) single spot Rf 0.5.

EXAMPLE 9

1-Methyl-N-$^3$-dimethyl-N$^5$-[3-[3-[(dimethylamino)methyl]phenoxy]propyl]-1H-1,2,4-triazole-3,5-diamine 1-Methyl-N$^5$-[3-[3-[(dimethylamino)methyl]phenoxy]propyl]-1H-1,2,4-triazole-3,5-diamine (1.1 g) was added portionwise to 98% formic acid (0.85 ml) at 5°. Formaldehyde solution (37%) was then added and the reaction mixture heated to 100°. After 12 hr the reaction was cooled, basified with potassium carbonate, and extracted with ethyl acetate. Distillation of the organic extract gave the title compound as a colourless oil (1.03 g) b.p. 180° (0.03 mm). TLC silica; ethyl acetate:isopropanol:water:0.88 ammonia (25:15:8:2) Rf 0.54.

Similarly prepared from 1-methyl-N$^5$-[3-[3-(1-piperidinylmethyl)phenoxy]propyl]-1H-1,2,4-triazole-3,5-diamine (1.0 g) was 1-methyl-N$^3$-dimethyl-N$^5$-[3-[3-(1-piperidinylmethyl)phenoxy]propyl]-1H-1,2,4-triazole-3,5-diamine (0.99 g) b.p. 223°/0.04 mm. TLC silica, methanol/0.88 ammonia 80:1, Rf 0.55.

EXAMPLE 10

(i)
1-Methyl-N$^3$-phenylmethylene-N$^5$-[3-[3-[(dimethylamino)methyl]phenoxy]propyl]-1H-1,2,4-triazole-3,5-diamine A mixture of 1-methyl-N$^5$-[3-[3-[(dimethylamino)methyl]phenoxy]propyl]-1H-1,2,4-triazole-3,5-diamine (6.08 g) and benzaldehyde (2.4 g) in dry benzene was heated under reflux during 12 hr in a Dean & Stark apparatus. The solvent was removed and the residue purified by column chromatography on silica using methanol to give the title compound as a yellow oil (7.4 g). TLC silica; methanol:ammonia (80:1) Rf 0.43. NMR (CDCl$_3$) 0.85 s (1H); 2.05 m (2H); 2.5–3.0 m (4H); 3.0–3.3 m (3H); 5.35 t (1H); 5.88 t (2H); 6.39 q (2H); 6.42 s (3H); 6.62 s (2H); 7.77 s (6H); 7.83 m (2H).

The following compounds were similarly prepared from the corresponding aldehyde and 1-methyl-N$^5$-[3-[3-[(dimethylamino)methyl]phenoxy]propyl]-1H-1,2,4-triazole-3,5-diamine, (A).

(ii) 3-Pyridinecarboxaldehyde (0.4 g) and (A) (1.0 g) gave 1-methyl-N$^3$-(3-pyridinylmethylene)-N$^5$-[3-[3-[(dimethylamino)methyl]phenoxy]propyl]-1H-1,2,4-triazole-3,5-diamine (1.23 g) m.p. 92°–3°. TLC Silica; methanol:ammonia (80:1) Rf 0.4.

(iii) 4-Pyridinecarboxaldehyde (0.4 g) and (A) (1.0 g) gave 1-methyl-N$^3$-(4-pyridinylmethylene)-N$^5$-[3-[3-[(dimethylamino)methyl]phenoxy]propyl]-1H-1,2,4-triazole-3,5-diamine (1.12 g) m.p. 127°–8°. TLC silica; methanol:ammonia (80:1) Rf 0.4.

EXAMPLE 11

(i)
1-Methyl-N$^3$-phenylmethyl-N$^5$-[3-[3-[(dimethylamino)methyl]phenoxy]propyl]-1H-1,2,4-triazole-3,5-diamine A mixture of 1-methyl-N$^3$-phenylmethylene-N$^5$-[3-[3-[(dimethylamino)methyl]phenoxy]propyl]-1H-1,2,4-triazole-3,5-diamine (2.0 g) and sodium borohydride (0.95 g) in methanol was stirred at 25° for 12 hr. The mixture was poured onto water and extracted with ethyl acetate. The organic extract was washed with brine and distilled to give the title compound as a pale yellow oil (1.4 g) b.p. 180° (0.04 mm). TLC silica; methanol:ammonia (80:1) Rf 0.7.

The following compounds were similarly prepared from the corresponding imine and sodium borohydride.

(ii) The 3-Pyridinylimine of Example 10(ii) (0.56 g) and sodium borohydride (0.075 g) gave 1-methyl-N$^3$-(3-pyridinylmethyl)-N$^5$-[3-[3-[(dimethylamino)methyl]phenoxy]propyl]-1H-1,2,4-triazole-3,5-diamine (0.43 g). TLC silica; methanol:ammonia (80:1) Rf 0.4. NMR (CDCl$_3$) 1.41 d (1H); 1.58 dd (1H); 2.30 dd (1H); 2.8 m (2H); 3–3.4 m (3H); 5.55 m (1H); 5.61 s (2H); 5.92 t (2H); 6.49 m (2H); 6.6 s (5H); 7.33 m (1H); 7.76 s (6H); 7.6–8.2 m (2H).

(iii) The 4-Pyridinylimine of Example 10 (iii) (0.5 g) and sodium borohydride (0.075 g) gave 1-methyl-N$^3$-(4-pyridinylmethyl)-N$^5$-[3-[3-[(dimethylamino)methyl]phenoxy]propyl]-1H-1,2,4-triazole-3,5-diamine (0.4 g) m.p. 110°–111°. TLC silica; methanol:ammonia (80:1) Rf 0.4.

EXAMPLE 12

1-Methyl-N$^5$-[3-[3-[(dimethylamino)methyl]phenylamino]propyl]-1H-1,2,4-triazole-3,5-diamine 3-[(3-Aminopropyl)amino]-N,N-dimethylbenzamide A mixture of 3-amino-N,N-dimethylbenzamide (15.4 g) and N-(3-bromopropyl)phthalimide (12 g) in dry xylene was heated under reflux during 12 hr. The precipitate that formed was dissolved in methanol and ethyl acetate added. The mixture was washed with water and the organic phase was evaporated to leave a crude oil (15 g) which was used without further purification.

The oil and hydrazine hydrate (5.55 g) were heated under reflux in ethanol for 2 hr and then cooled to 25°. A solid precipitate that formed was removed by filtration and the filtrate concentrated in vacuo to give the title compound (2.2 g) b.p. 170°–5°, (0.01 mm). TLC silica; methanol:ammonia (80:1) Rf 0.2.

3-[[3-[(3-Amino-1-methyl-1H-1,2,4-triazol-5-yl)amino]propyl]-amino]-N,N-dimethylbenzamide 3-[(3-Aminopropyl)amino]-N,N-dimethylbenzamide (0.8 g) and N-cyano-1-methyl-2-(phenylmethylene)hydrazine carboximidothioic acid, methyl ester (0.84 g) were heated together under reduced pressure of 14 mm Hg during 4 hr at 100°. The cooled reaction mixture was dissolved in acetone, treated with 1 N hydrochloric acid (2 ml) and heated at 60° for 0.5 hr. The mixture was cooled, basified with potassium carbonate and extracted with ethyl acetate. Evaporation of the organic extracts gave a viscous oil which was triturated with ether to give the title compound (0.49 g). TLC silica; methanol:ammonia (80:1) Rf 0.63. NMR (CDCl$_3$) 2.9 m (1H); 3.2–3.7 m (3H); 5.28 t (1H); 6.12 s (2H); 6.7 s (3H); 7.0 s (6H); 6.4–7.4 m (5H); 8.23 t (2H).

1-Methyl-N$^5$-[3-[3-[(dimethylamino)methyl]phenylamino]propyl]-1H-1,2,4-triazole-3,5-diamine A mixture of 3-[[3-[(amino-1-methyl-1H-1,2,4-triazol-5-yl)amino]propyl]amino]-dimethylbenzamide (0.47 g) and lithium aluminium hydride (0.15 g) in dry tetrahydrofuran was stirred at 25° for 12 hr. Water was added and the reaction mixture was filtered. The filtrate was evaporated and the residue purified by column chromatography on silica using methanol to give the title compound as a buff coloured solid (0.07 g) m.p. 101°–2°. TLC silica; methanol:ammonia (80:1) Rf 0.53.

EXAMPLE 13

1-Methyl-$N^5$-[3-[3-[1-piperidinylmethyl]phenoxy]-propyl]-1H-1,2,4-triazole-3,5-diamine 3-[3-[1-Piperidinylmethyl]phenoxy]propanamine (2.48 g) and N-cyano-1-methyl-2-(phenylmethylene) hydrazine carboximidothioic acid, methyl ester (2.32 g) were heated at 70° under water-pump vacuum for 4 hr. Acetone was added and the solution was treated with dilute hydrochloric acid for 1 hr, washed with ether, basified and extracted with ethyl acetate. Evaporation of the ethyl acetate extracts gave an oil which crystallised from toluene/ether to give the title compound as a white solid (0.98 g) m.p. 94°–5°. TLC silica, methanol/0.88 ammonia 80:1, Rf 0.5.

EXAMPLE 14

1-Methyl-$N^5$-[3-[3-[1-(1,2,3,6-tetrahydropyridinyl)methyl]phenoxy]propyl]-1H-1,2,4-triazole-3,5-diamine A solution of N'-cyano-N-[3-[3-(1,3-dioxolan-2-yl)phenoxy]propyl]-1-methyl-2-(phenylmethylene) hydrazinecarboximidamide (2.62 g) in tetrahydrofuran (40 ml) was stirred at room temperature for 0.5 h with 2 N hydrochloric acid (5 ml). The mixture was treated with 1,2,3,6-tetrahydropyridine (9 ml) and stirred at room temperature for a further 1 h. The mixture was treated with sodium borohydride (1.5 g), stirred at room temperature for 18 h, diluted with ethyl acetate, filtered and the filtrate evaporated in vacuo. The resulting oil was partitioned between ethyl acetate and water. The organic phase was evaporated in vacuo and the residue was purified by column chromatography on silica, using methanol. Evaporation of the eluates gave the title compound which was recrystallised from a mixture of benzene and cyclohexane (1.26 g) m.p. 102°–3°. TLC silica; methanol-ammonia 80:1; Rf 0.6.

The following compounds were similarly prepared from N'-cyano-N-[3-[3-(1,3-dioxolan-2-yl)phenoxy]propyl]-1-methyl-2-(phenylmethylene) hydrazine carboximidamide (A) and the corresponding amine.

(ii) (A) (3.00 g) and 4-methylpiperidine (10 ml) gave 1-methyl-$N^5$-[3-[3-[1-(4-methylpiperidinyl)methyl]-phenoxy]propyl]-1H-1,2,4-triazole-3,5-diamine (1.67 g) m.p. 133°–4°. TLC silica; methanol:ammonia 80:1; Rf 0.7.

(iii) (A) (2.70 g) and cyclohexylamine (10 ml) gave 1-methyl-$N^5$-[3-[3-[(cyclohexylamino)methyl]phenoxy]propyl]-1H-1,2,4-triazole-3,5-diamine (1.03 g) m.p. 102°–3°. TLC silica, methanol:ammonia 80:1; Rf 0.7.

(iv) (A) (3.12 g) and heptamethyleneimine (10 g) gave 1-methyl-$N^5$-[3-[3-[(1-heptamethyleneiminyl)methyl]-phenoxy]propyl]-1H-1,2,4-triazole-3,5-diamine (0.63 g) m.p. 71°–3°. TLC silica; methanol:ammonia 80:1; Rf 0.6.

(v) (A) (1.74 g) and allylamine (10 ml) gave 1-methyl-$N^5$-[3-[3-[(2-propen-1-amino)methyl]phenoxy]propyl]-1H-1,2,4-triazole-3,5-diamine (0.47 g) m.p. 71°–2°. TLC silica; methanol:ammonia 80:1; Rf 0.6.

(vi) (A) (2.42 g) and benzylamine (10 ml) gave 1-methyl-$N^5$-[3-[3-[[(phenylmethyl)amino]methyl]-phenoxy]propyl]-1H-1,2,4-triazole-3,5-diamine (1.44 g) m.p. 90°–1°. TLC silica; methanol:ammonia 80:1; Rf 0.8.

(vii) (A) (3.43 g) and n-propylamine (10 ml) gave 1-methyl-$N^5$-[3-[3-[(1-propylamino)methyl]phenoxy]-propyl]-1H-1,2,4-triazole-3,5-diamine (0.2 g) m.p. 79°–81°. TLC silica; ethyl acetate:isopropanol:water-:ammonia 25:15:8:2; Rf 0.7.

(viii) (A) (3.2 g) and morpholine (10 ml) gave 1-methyl-$N^5$-[3-[3-(4-morpholinylmethyl)phenoxy]propyl]-1H-1,2,4-triazole-3,5-diamine (0.74 g) m.p. (hydrochloride salt) 55° (softens). TLC silica, ethyl acetate/water-/isopropanol/0.88 ammonia 25:8:15:2, Rf 0.48.

(ix) (A) (2.2 g) and 2,6-dimethylmorpholine (10 ml) gave 1-methyl-$N^5$-[3-[3-[4-(2,6-dimethylmorpholinyl)-methyl]phenoxy]propyl]-1H-1,2,4-triazole-3,5-diamine (0.3 g) m.p. (hydrochloride salt) 60° (softens). TLC silica, ethyl acetate/water/isopropanol/0.88 ammonia 25:8:15:2, Rf 0.5.

(x) (A) (3.2 g) and N,N-dimethylethylenediamine (5.5 ml) gave 1-methyl-$N^5$-[3-[3-[(4,4-dimethylaminoethylamino)methyl]phenoxy]propyl]-1H-1,2,4-triazole-3,5-diamine (1.1 g) b.p. 250°/0.04 mm. TLC silica ethyl acetate/water/isopropanol/0.88 ammonia 25:8:15:2, Rf 0.3.

(xi) (A) (1.98 g) and heptylamine (15 ml) gave 1-methyl-$N^5$-[3-[3-[(heptylamino)methyl]phenoxy]propyl]-1H-1,2,4-triazole-3,5-diamine (0.21 g) m.p. 64°–65°. TLC silica, ethyl acetate/water/isopropanol/0.88 ammonia 25:8:15:2, Rf. 0.5.

(xii) (A) (2.47 g) and isobutylamine (10 ml) gave 1-methyl-$N^5$-[3-[3[(2-methylpropylamino)methyl]-phenoxy]propyl]-1H-1,2,4-triazole-3,5-diamine (1.23 g) m.p. 89°–90°. TLC silica, methanol/0.88 ammonia 80:1, Rf 0.6.

(xiii) (A) (2.0 g) and 2-methoxyethanamine (20 ml) gave 1-methyl-$N^5$-[3-[3-[[(2-methoxyethyl)amino]methyl]phenoxy]propyl]-1H-1,2,4-triazole-3,5-diamine (0.5 g) m.p. 61°–62.5°. TLC silica, ethyl acetate/water/isopropanol/0.88 ammonia 25:8:15:2, Rf 0.58.

(xiv) (A) (4.4 g) and n-butylamine (20 ml) gave 1-methyl-$N^5$-[3-[3-[(butylamino)methyl]phenoxy]propyl]-1H-1,2,4-triazole-3,5-diamine (0.3 g) m.p. 99.5°–101°. TLC silica; ethyl acetate, water, isopropanol, 0.88 ammonia 25:8:15:2, Rf 0.45.

EXAMPLE 15

1-Methyl-3-(1-pyrrolidinyl)-$N^5$-[3-[3-[(dimethylamino)methyl]phenoxy]propyl]-1H-1,2,4-triazole-5-amine 1-Methyl-3-chloro-$N^5$-[3-[3-[(dimethylamino)methyl]-phenoxy]propyl]-1H-1,2,4-triazole-5-amine A solution of sodium nitrite (0.46 g) in water (1.5 ml) was added dropwise to a solution of 1-methyl-$N^5$-[3-[3-[(dimethylamino)methyl]phenoxy]propyl]-1-H-1,2,4-triazole-3,5-diamine (2.0 g) in concentrated hydrochloric acid at 5°. This solution of the diazonium salt was added to a solution of cuprous chloride at 75° [prepared by adding a solution of sodium metabisulphite (0.41 g) and sodium hydroxide (0.27 g) in water (3 ml) to a hot solution of copper sulphate (1.89 g) and sodium chloride (1.61 g) in water (6 ml)].

Concentrated hydrochloric acid (84 ml) was added to the reaction mixture which was allowed to stand at 25° for 12 h, cooled, basified with sodium bicarbonate and extracted with ethyl acetate. Distillation of the organic extract gave the title compound as a pale yellow oil (1.23 g) b.p. 225° (0.04 mm). TLC silica; methanol:0.88 ammonia 80:1; Rf 0.64.

1-Methyl-3-(1-pyrrolidinyl)-$N^5$-[3-[3-[(dimethylamino)-methyl]phenoxy]propyl]-1H-1,2,4-triazole-5-amine A mixture of 1-methyl-3-chloro-$N^5$-[3-[3-[(dimethylamino)methyl]phenoxy]propyl]-1H-1,2,4-triazole-5-amine (0.4 g), pyrrolidine (0.71 g) and sodium iodide (0.3 g) was heated at 180° in an autoclave for 16 hr. The reaction mixture was dissolved in dilute hydrochloric acid, washed with ethyl acetate, basified with sodium hydroxide and extracted with toluene. The toluene extracts were fractionally distilled to give the title compound as a pale yellow oil (0.27 g) b.p. 210° (0.04 mm). TLC silica; ethyl acetate:isopropanol:water:0.88 ammonia 25:15:8:2; Rf 0.6.

EXAMPLE 16

(i)
1-Methyl-$N^3$-diethyl-$N^5$-[3-[3-[(dimethylamino)methyl]phenoxy]propyl]-1H-1,2,4-triazole-3,5-diamine 1-Methyl-$N^5$-[3-[3-[(dimethylamino)methyl]phenoxy]propyl]-1H-1,2,4-triazole-3,5-diamine (1.0 g) and acetaldehyde (10 ml) were hydrogenated at room temperature and atmospheric pressure in ethanol over 10% palladium on charcoal. The catalyst was removed by filtration and the filtrate distilled to give the product as a pale yellow oil (0.95 g) b.p. 190° (6×10$^{-2}$ mm). TLC silica; methanol:0.88 ammonia 80:1; Rf 0.58.

Similarly prepared from 1-methyl-$N^5$-[3-[3-[(dimethylamino)methyl]phenoxy]propyl]-1H-1,2,4-triazole-3,5-diamine (0.5 g) and propionaldehyde (3 ml) was 1-methyl-$N^3$-dipropyl-$N^5$-[3-[3-[(dimethylamino)methyl]phenoxy]prpyl]-1H-1,2,4-triazole-3,5-diamine (0.5 g) b.p. 200°/0.06 mm. TLC silica, methanol/0.88 ammonia 80:1, Rf 0.53.

EXAMPLE 17

(i)
1-Methyl-$N^5$-[3-[3-[2-(dimethylamino)ethyl]phenoxy]propyl]-1H-1,2,4-triazole-3,5-diamine 3-[3-(Aminopropoxy)]-N,N-dimethylbenzeneethanamine (0.36 g) and N-cyano-1-methyl-2-(phenylmethylene) hydrazinecarboximidothioic acid methyl ester (0.37 g) were heated at reflux in toluene for 4 h. The cooled solution was treated with dilute hydrochloric acid (5 ml) for 1 h, washed with ethyl acetate, basified and extracted with ethyl acetate. The organic extract was evaporated to give the title compound as a white solid (0.1 g) after recrystallisation from toluene, m.p. 81°–2°. TLC silica; ethyl acetate:isopropanol:water:0.88 ammonia; 25:15:8:2; Rf 0.35.

The following compounds were similarly prepared from the corresponding diamine and the appropriate N-cyano-1-alkyl-2-(phenylmethylene) hydrazine carboximidothioic acid methyl ester (A).

(ii) Diamine (0.6 g) and A (0.55 g) gave 1-methyl-$N^5$-[2-[[[4-methyl-5-(1-pyrrolidinylmethyl)-2-furanyl]methyl]thio]ethyl]-1H-1,2,4-triazole-3,5-diamine (0.45 g). NMR (CDCl$_3$) 4.03, s (1H); 6.38 s (2H); 6.52 s (2H); 6.6, s+t (5H); 7.30 t (2H); 7.52 m (4H); 8.10 s (3H); 8.31 m (4H); C$_{16}$H$_{26}$N$_6$OS requires C, 54.83; H, 7.48; N, 23.98%.

Assay found C, 54.95; H, 7.85; N, 23.89%.

(iii) Diamine (0.82 g) and A (0.81 g) gave 1-methyl-$N^5$-[2-[3-[2-(dimethylamino)ethyl]phenoxy]ethyl]-1H-1,2,4-triazole-3,5-diamine (0.22 g) m.p. 72°. TLC silica, methanol/0.88 ammonia 80:1, Rf 0.3.

EXAMPLE 18

1-Methyl-$N^3$-ethyl-$N^5$-[3-[3-[(dimethylamino)methyl]phenoxy]propyl]-1H-1,2,4-triazole-3,5-diamine N-[5-[[3-[3-[(Dimethylamino)methyl]phenoxy]propyl]amino]-1-methyl-1H-1,2,4-triazol-3-yl]acetamide A mixture of 1-methyl-$N^5$-[3-[3-[(dimethylamino)methyl]phenoxy]propyl]-1H-1,2,4-triazole-3,5-diamine (1.0 g), acetic anhydride (0.35 g) and pyridine (50 ml) was stirred at 25° for 12 h. The pyridine was removed and the residue was dissolved in ethyl acetate. The organic solution was washed with aqueous sodium carbonate and evaporated to give the title compound as a pale yellow oil (1.1 g). TLC silica, methanol/0.88 ammonia 80:1, Rf 0.49. NMR (CDCl$_3$) 1.42 brs (1H); 2.81 m (1H); 3–3.4 m (3H); 5.34 t (1H); 5.98 t (2H); 6.52 s (3H); 6.65 s (2H); 6.5 m (2H); 7.8 s (6H); 7.5–8.1 m (2H); 7.9 s (3H).

1-Methyl-$N^3$-ethyl-$N^5$-[3-[3-[(dimethylamino)methyl]phenoxy]propyl]-1H-1,2,4-triazole-3,5-diamine A mixture of N-[5-[[3-[3-[(dimethylamino)methyl]phenoxy]propyl]-amino]-1-methyl-1H-1,2,4-triazol-3-yl]acetamide (1.1 g), lithium aluminium hydride (0.15 g) and tetrahydrofuran (20 ml) was heated at reflux for 12 h under a nitrogen atmosphere. The mixture was quenched with water (5 ml), filtered and the filtrate distilled to give the title compound as a pale yellow oil (0.6 g) b.p. 220°/0.06 mm. TLC silica, methanol/0.88 ammonia 80:1, Rf 0.54.

EXAMPLE 19

1-Methyl-$N^3$-methyl-$N^5$-[3-[3-[(dimethylamino)methyl]phenoxy]propyl]-1H-1,2,4-triazole-3,5-diamine 5-[[3-[3-[(Dimethylamino)methyl]phenoxy]propyl]amino]-1-methyl-1H-1,2,4-triazole-3-carbamic acid, ethyl ester A mixture of 1-methyl-$N^5$-[3-[3-[(dimethylamino)methyl]phenoxy]propyl]-1H-1,2,4-triazole-3,5-diamine (2.0 g), ethyl chloroformate (0.72 g) and dimethylformamide (30 ml) was stirred at 25° for 12 h. The suspension was diluted with water (100 ml) and extracted with ethyl acetate. The organic extracts were evaporated to leave the title compound as a pale yellow oil (2.1 g). TLC silica, methanol/0.88 ammonia 80:1, Rf 0.61. NMR (D$_2$O 2.52 t (1H); 2.8–3 m (3H); 5.42 s (2H); 5.6–6 m (6H); 6.48 t (2H); 6.5 s (3H); 7.09 s (6H); 7.88 m (2H); 8.67 t (3H).

1-Methyl-$N^3$-methyl-$N^5$-[3-[3-[(dimethylamino)methyl]phenoxy]propyl]-1H-1,2,4-triazole-3,5-diamine A mixture of 5-[[3-[3-[(dimethylamino)methyl]phenoxy]propyl]amino]-1-methyl-1H-1,2,4-triazole-3-carbamic acid, ethyl ester (0.35 g) lithium aluminium hydride (0.13 g) and tetrahydrofuran (10 ml) was heated under reflux for 48 h. The mixture was quenched with water (0.5 ml), filtered and the filtrate was evaporated. The residue was purified by column chromatography on silica with methanol as the eluant to give the title compound as a pale yellow oil (0.1 g). TLC silica; methanol/0.88 ammonia 80:1, Rf 0.43. NMR (CDCl$_3$) 2.78 t (1H); 3.0–3.3 m (3H); 5.47 s (1H); 5.95 t+brs (3H); 6.50 q (2H); 6.6 s (5H); 7.17 t (3H); 7.78 s (6H); 7.93 m (2H).

EXAMPLE 20

(i)
1-(2-Hydroxyethyl)-$N^5$-[3-[3-[(dimethylamino)methyl]phenoxy]propyl]-1H-1,2,4-triazole-3,5-diamine A mixture of N-cyanocarbonimidodithioic acid, dimethyl ester (2.92 g) and 2-hydroxyethyl hydrazine (1.52 g) in acetonitrile (50 ml) was stirred at 25° for 12 h. The solvent was removed at 25° to give a pale yellow oil (3.4 g) which was used without further purification.

The oil (3.4 g) and benzaldehyde (2.12 g) were stirred at 30° for 2 h and the resulting mixture triturated with ether to leave a solid (4.15 g), which was used without further purification.

The solid (2.0 g) was heated with 3-(3-aminopropoxy)-N,N-dimethylbenzenemethanamine (1.59 g) at 60° under water pump vacuum during 3 h to give a tarry residue which was washed with ether and extracted with ethyl acetate. The ethyl acetate extract was evaporated and the residue was dissolved in acetone (50 ml). 2 N Hydrochloric acid was added and the solution stirred at 25° for 1 h. The solvent was removed and the residue partitioned between water (25 ml) and ethyl acetate (25 ml). The aqueous phase was separated, treated with 2 N sodium hydroxide and extracted with ethyl acetate. The organic extracts were evaporated and the residue purified by column chromatography using methanol as eluant to give the title compound as a white crystalline solid (0.14 g) m.p. 105°–6°. TLC silica, methanol/0.88 ammonia 80:1 Rf 0.36.

(ii) Similarly prepared from 3-[3-(1-piperidinylmethyl)phenoxy]propylamine (1.7 g) was 1-(2-hydroxyethyl)-$N^5$-[3-[3-(1-piperidinylmethyl)phenoxy]propyl]-1H-1,2,4-triazole-3,5-diamine (0.1 g) m.p. 90°–1°. TLC Silica, methanol:0.88 ammonia 80:1, Rf 0.37.

EXAMPLE 21

1-Methyl-$N^5$-[3-[3-[1-piperidinylmethyl]phenoxy]propyl]-1H-1,2,4-triazole-3,5-diamine, salt with succinic acid (2:1), hydrate A solution of 1-methyl-$N^5$-[3-[3-[1-piperidinylmethyl]phenoxy]propyl]-1H-1,2,4-triazole-3,5-diamine (34 g) in ethyl acetate (85 ml) was added to a solution of succinic acid (5.9 g) in boiling ethanol (80 ml). The mixture was cooled, stirred at room temperature for 1 hr and filtered to give the title compound as a white crystalline solid (33.1 g) m.p. 118°–121°. UV data: $E^1$ in water at 267 nm=46.2.

EXAMPLE 22

1-Methyl-$N^3$-[5-hydroxypentyl]-$N^5$-[3-[3-[(dimethylamino)methyl]phenoxy]propyl]-1H-1,2,4-triazole-3,5-diamine 1-Methyl-$N^5$-[3-[3-[(dimethylamino)methyl]phenoxy]propyl]-1H-1,2,4-triazole-3,5-diamine (1.0 g) and 5-hydroxypentanal (1.9 ml) were heated at reflux in ethanol (30 ml) for 5 h. The solution was cooled at 5° and treated with sodium borohydride (0.76 g). The resulting suspension was stirred at room temperature for 16 h, treated with water and reduced in volume in vacuo. The aqueous solution was extracted with ethyl acetate, and the organic extracts were distilled to give the title compound as a pale yellow oil (0.47 g) b.p. 250°/0.5 mm. TLC silica; ethyl acetate:isopropanol:water: 0.88 ammonia 25:15:8:2, Rf 0.6.

EXAMPLE 23

1-Methyl-$N^5$-[3-[3-(1-piperidinylmethyl)phenoxy]propyl]-1H-1,2,4-triazole-3,5-diamine A solution of 3-[3-[(3-amino-1-methyl-1H-1,2,4-triazol-5-yl)amino]propoxy]-N,N,N-trimethylbenzenemethanium iodide (1 g) and piperidine (2.14 ml) in water (1 ml) was heated under reflux for 8 h. The solution was evaporated to give an oil which was purified by column chromatography using methanol as eluant to give the title compound as a white solid (0.36 g) m.p. 93°–94°. TLC silica, methanol/0.88 ammonia 80:1, Rf 0.6.

EXAMPLE 24

Following the method of Example 7:

(i) Diamine (2.0 g) and A (1.96 g) gave 1-methyl-$N^5$-[3-[3-[(diethylamino)methyl]phenoxy]propyl]-1H-1,2,4-triazole-3,5-diamine (0.25 g) m.p. 68°–9°. TLC silica, ethyl acetate/water/isopropanol/0.88 ammonia 25:8:15:2, Rf 0.7.

(ii) Diamine (0.23 g) and A (0.23 g) gave 1-methyl-$N^5$-[3-[3-[3-(dimethylamino)propyl]phenoxy]propyl]-1H-1,2,4-triazole-3,5-diamine (0.12 g) m.p. 64°–65.5°. TLC silica, ethyl acetate/water/isopropanol/0.88 ammonia 25:8:15:2, Rf 0.3.

EXAMPLE 25

Following the method of Example 14:

(i) A (1.92 g) and 0.88 ammonia (10 ml) gave 1-methyl-$N^5$-[3-[3-(aminomethyl)phenoxy]propyl]-1H-1,2,4-triazole-3,5-diamine (0.15 g). TLC silica, methanol/0.88 ammonia 80:1, Rf 0.5 NMR (d4 MeOH) 2.77 t (1H); 3.0–3.3 m (3H); 5.95 t (2H); 6.30 s (2H); 6.57 q (2H); 6.65 s (3H); 7.95 m (2H).

(ii) A (2.5 g) and propargylamine (5 ml) gave 1-methyl-$N^5$-[3-[3-[(2-propynylamino)methyl]phenoxy]propyl]-1H-1,2,4-triazole-3,5-diamine (0.43 g). NMR (CDCl₃) 2.72 t (1H); 3.0–3.3 m (3H); 5.41 t (1H); 5.90 t (2H); 5.97 brs (2H); 6.15 s (2H); 6.48 q (2H); 6.58 d (2H); 6.60 s (3H); 7.72 t (1H); 7.92 m (2H). TLC silica, ethyl acetate/water/isopropanol/0.88 ammonia 25:8:15:2, Rf 0.67.

EXAMPLE 26

1-Methyl-$N^5$-[3-[3-[1-(4-hydroxypiperidinyl)methyl]phenoxy]propyl]-1H-1,2,4-triazole-3,5-diamine Following the method of Example 17, the appropriate diamine (1.0 g) and A (0.23 g) gave the title compound (0.3 g) m.p. hydrochloride salt 148° (dec). TLC ethyl acetate/water/isopropanol/0.88 ammonia 25:8:15:2, Rf 0.6.

EXAMPLE 27

1-Methyl-$N^5$-[3-[3-(1-piperidinylmethyl)phenoxy]propyl]-1H-1,2,4-triazole-3,5-diamine A solution of 3-[3-[[[(cyanimino)[1-methyl-2-(phenylmethylene)hydrazino]]methyl]amino]propoxy]-N,N,N-trimethylbenzenemethanium iodide (1.07 g) and piperidine (1.7 g) in water (1 ml) was heated under reflux for 24 hr. The water was removed to give an oil which was purified by column chromatography using methanol/0.88 ammonia 80:1 as eluent to give the title compound as a white solid (0.2 g), m.p. 94°–95°. TLC silica, methanol/0.88 ammonia 80:1, Rf 0.6.

EXAMPLE 28

1-Methyl-$N^5$-[3-[3-(1-piperidinylmethyl)phenoxy]propyl]-1H-1,2,4-triazole-3,5-diamine 3-[3-[(1-Methyl-3-amino-1H-1,2,4-triazol-5-yl)amino]propoxy]benzenemethanol, hydrochloride N'-Cyano-N-[3-[3-(1,3-dioxolan-2-yl)phenoxy]propyl]-1-methyl-2-(phenylmethylene)hydrazinecarboximidamide (18.2 g) in tetrahydrofuran (150 ml) was treated with 5 N hydrochloric acid (30 ml) at 30° C. for 30 mins. Triethylamine (20 ml) was added followed by sodium borohydride (8.0 g). The resulting mixture was stirred at room temperature for 14 hrs, diluted with ethyl acetate (150 ml) and evaporated to a red oil which was dissolved in ethyl acetate, washed with sodium bicarbonate solution and evaporated to leave an oil. This oil was treated with etheral hydrogen chloride to give the title compound as a white solid (8 g). m.p. 148°–9°. TLC silica, ethyl acetate, water, isopropanol 0.88 ammonia (25:8:15:2) Rf 0.56.

1-Methyl-$N^5$-[3-[3-(bromomethyl)phenoxy]propyl]-1H-1,2,4-triazole-3,5-diamine, hydrobromide A solution of 3-[3-[(1-methyl-3-amino-1H-1,2,4-triazol-5-yl)amino]propoxy]benzene methanol (1.9 g) in methylene chloride (25 ml) was treated with phosphorus tribromide (3.27 g) at room temperature for 76 hrs. The resulting oil was purified by column chromatography using ethyl acetate/methanol, 8:1 as eluant to yield the title compound as a white solid (1.7 g). TLC silica ethyl acetate, water, isopropanol 0.88 ammonia (25:8:15:2) Rf 0.72. m.p. 129°–130°.

1-Methyl-$N^5$-[3-[3-(1-piperidinylmethyl)phenoxy]propyl]-1H-1,2,4-triazole-3,5-diamine 1-Methyl-$N^5$-[3-[3-(bromomethyl)phenoxy]propyl]-1H-1,2,4-triazole-3,5-diamine, hydrobromide (0.3 g) was dissolved in ethanol (5 ml) and treated with piperidine (0.3 g) at room temperature. The solvent was evaporated in vacuo and the residue triturated with ethyl acetate to afford the title compound as a white crystalline solid (0.22 g).

TLC silica, ethyl acetate, water, isopropanol 0.88 ammonia (25:8:15:2) Rf 0.5, m.p. 93°–94° C.

EXAMPLE 29

$N^3$-[3-[3-(1-Piperidinylmethyl)phenoxy]propyl]-1H-1,2,4-triazole-3,5-diamine

[3-[3-(1-Piperidinylmethyl)phenoxy]propyl]isothiocyanate

A solution of carbon disulphide (3.3 ml) in acetone (8 ml) was added dropwise to a solution of 3-[3-(1-piperidinylmethyl)phenoxy propanamine (12.4 g) in acetone (30 ml) over a 15 minute period, between −5° and −10° C. The solution was cooled to −14° C. and mercury (II) chloride (13.6 g) in acetone (30 ml) was added, during 45 minutes. Triethylamine (16 ml) was added at 0° C. during 15 minutes, and the mixture was heated at reflux for 45 minutes. The resulting suspension was purified by filtration and the filtrate evaporated in vacuo. The residue was purified by column chromatography using methanol as eluant to give the title compound (6 g) as an amber oil.

TLC silica/methanol Rf 0.4.

Assay: Found C, 65.9; H, 7.7; N, 9.6; S, 11.1; $C_{16}H_{22}N_2OS$ requires: C, 66.2; H, 7.6; N, 9.6; S, 11.0%.

$N^3$-[3-[3-(piperidinylmethyl)phenoxy]propyl]-1H-1,2,4-triazole-3,5-diamine

A mixture of [3-[3-(1-Piperidinylmethyl)phenoxy]propyl]-isothiocyanate (0.9 g) and aminoguanidine (0.45 g) was heated at 140°–160° for 3 hours. The resulting mixture was purified by column chromatography using ethyl acetate:ethanol:0.88 ammonia (100:10:1) as eluant to afford the title compound (0.1 g) m.p. 100–101.5. TLC silica/ethylacetate/ethanol/0.88 ammonia 10:1:1 Rf 0.3.

EXAMPLE 30

1-Methyl-$N^5$-[3-[[5-(dimethylamino)methyl]-2-furanyl]methoxy]propyl]-1H-1,2,4-triazole-3,5-diamine A mixture of 5-[(dimethylamino)methyl]-2-furanmethanol (0.31 g), 1-methyl-$N^5$-(3-hydroxypropyl)-1H-1,2,4-triazole-3,5-diamine (0.72 g) and methanesulphonic acid (1.2 ml) in dry tetrahydrofuran (20 ml) was stirred at 25° for 3 h and then at reflux for 8 h. The cooled mixture was diluted with water (10 ml), treated with anhydrous potassium carbonate and extracted with ethyl acetate. The combined extracts were evaporated and the residue was purified by column chromatography with methanol as eluant to give the title compound as a yellow oil (0.1 g). NMR (CDCl$_3$) 3.75 d (1H); 3.86 d (1H); 5.20 t (1H); 5.58 s (2H); 6.00 br.s (2H); 6.40 t (2H); 6.60 s (2H); 6.62 q (2H); 6.73 s (3H); 7.76 s (6H); 8.12 m (2H). TLC silica, methanol/0.88 ammonia 79:1, Rf 0.5.

EXAMPLE 31

1-Methyl-$N^5$-[3-[3-(1-piperidinylmethyl)phenoxy]propyl]-1H-1,2,4-triazole-3,5-diamine 1-Methyl-$N^5$-[3-[3-(1,3-dioxolan-2-yl)phenoxy]propyl]-1H-1,2,4-triazole-3,5-diamine A solution of $N'$-cyano-N-[3-(1,3-dioxolan-2-yl)phenoxy]propyl]-1-methyl-2-phenylmethylene hydrazine carboximidamide (2.50 g) in piperidine (6 ml) was heated under reflux for 70 h. The mixture was evaporated in vacuo, and the resulting oil was chromatographed on silica. Elution with a mixture of methanol and ethyl acetate (1:1) gave an oil which was crystallised from a mixture of benzene and cyclohexane, to give the title compound (0.29 g) m.p. 117°–8°. TLC silica (methanol) Rf 0.7.

1-Methyl-$N^5$-[3-[3-(1-piperidinylmethyl)phenoxy]propyl]-1H-1,2,4-triazole-3,5-diamine A solution of 1-methyl-$N^5$-[3-[3-(1,3-dioxolan-2-yl)phenoxy]propyl]-1H-1,2,4-triazole-3,5-diamine (106 mg) in tetrahydrofuran (2 ml) was stirred with 2 N hydrochloric acid (0.2 ml) for ½ h at room temperature. The mixture was treated with piperidine (0.5 ml), stirred at room temperature for 1 h, and then treated with sodium borohydride (75 mg). After a further 1 h, the mixture was diluted wit water, and extracted with ethyl acetate. The combined extracts were dried and evaporated in vacuo. The resulting oil was crystallized from a mixture of benzene and cyclohexane to yield the title compound (60 mg) m.p. 93°–4°. TLC silica (methanol:ammonia 80:1) Rf 0.5.

EXAMPLE 32

$N^5$-[4-[3-(1-Piperidinylmethyl)phenoxy]butyl]1H-1,2,4-triazole-3,5-diamine

4-[3-(1-piperidinylmethyl)phenoxy]butanitrile

3-[1-Piperidinylmethyl]phenol (11.2 g) was added to a stirred suspension of sodium hydride (1.5 g) in dry dimethylformamide (60 ml) at room temperature. The mixture was stirred at room temperature for 5 h, and treated with 4-bromobutanitrile (9 g). After a further 24 h at room temperature, the mixture was poured onto ice and extracted with ethyl acetate. The combined extracts were washed with water and evaporated in vacuo. The residual oil was distilled under reduced pressure to yield the title compound (14.8 g) b.p. 200°/0.06 mm. TLC silica (methanol:ammonia 80:1) Rf 0.8.

4-[3-(1-Piperidinylmethyl)phenoxy]butanal, semicarbazone

A solution of 4-[B 3-(1-piperidinylmethyl)phenoxy]-butanitrile (5.16 g), sodium acetate (7.38 g) and semicarbazide hydrochloride (7.76 g) in ethanol (60 ml) and water (60 ml) was hydrogenated over Raney nickel (12 g) at room temperature and one atmosphere. The mixture was filtered, and reduced to a volume of 50 ml in vacuo. The resulting solution was diluted with water, basified with potassium carbonate and extracted with ethyl acetate. The organic extracts were evaporated to give an oil which was chromatographed on silica with methanol as the eluant to give the title compound as a colourless oil. (4.4 g) TLC silica (methanol:ammonia 80:1) Rf 0.7. NMR (CDCl$_3$) 0.28 bs, (1H); 2.6–2.9 m, (2H); 3.0–3.4 m (3H); 4.4 bs (2H); 6.02 t (2H); 6.57 s (2H); 7.4–8.9 m (14H).

4-[3-(1-Piperidinylmethyl)phenoxy]butanal

A solution of 4-[3-(1-piperidinylmethyl)phenoxy]-butanal, semicarbazone (4.34 g) in 2 N hydrochloric acid (40 ml) was stirred with 37% aqueous formaldehyde solution (40 ml) for 1 h at room temperature. The mixture was diluted with water, treated with potassium carbonate and extracted with ethyl acetate. The combined organic extracts were evaporated in vacuo and the residual oil was chromatographed on silica with methanol as eluant to give the title compound (1.93 g) as a colourless oil. TLC silica (methanol) Rf 0.5, NMR (CDCl$_3$) 0.1 t (1H); 2.75 t (1H); 3.0–3.3 m (3H); 6.02 t (2H); 6.55 s (2H); 7.35 m (2H); 7.5–7.7 m (4H); 7.88 m (2H); 8.2–8.6 m (6H).

N$^5$-[4-[3-(1-Piperidinylmethyl)phenoxy]butyl]-1H-1,2,4-triazole-3,5-diamine A solution of 4-[3-(1-piperidinylmethyl)phenoxy]-butanal (522 mg) and 3,5-diamino-1,2,4-triazole (200 mg) in absolute ethanol (20 ml) was heated under reflux for 2 h. The cooled solution was treated with sodium borohydride (200 mg) and stirred at room temperature for 18 hr. The mixture was evaporated in vacuo and the residue partitioned between ethyl acetate and water. The combined organic extracts were evaporated in vacuo and the residue was chromatographed on silica with methanol as eluant to give the title compound as an oil (250 mg), TLC silica (ethyl acetate:isopropanol:water:ammonia 25:15:8:2) 0.4, NMR (CDCl$_3$) 2.8 t (1H); 3.0–3.3 m (3H); 5.3 m (2H); 6.2 m (2H); 6.6–6.8 m (4H); 7.7 m (4H); 8.0–8.8 m (10H).

EXAMPLE 33

1-Methyl-N$^3$-[2-methoxyethyl]-N$^5$-[3-[3-(1-piperidinylmethyl)phenoxy]propyl]-1H-1,2,4-triazole-3,5-diamine 1-Methyl-N$^5$[3-[3-(1-piperidinylmethyl)phenoxy]propyl]-1H-1,2,4-triazole-3,5-diamine (2.39 g) and methoxyacetaldehyde diethylacetal (2.96 g) were heated at reflux in ethanol (50 ml) and 2 N hydrochloric acid (10 ml) for 24 hr.

The cooled reaction mixture treated with sodium borohydride (7.6 g) and stirred at room temperature for 24 hr. The suspension was treated with water, filtered, and the filtrate was extracted with ethyl acetate. The organic extracts were distilled to give the title compound as a yellow oil (0.2 g). b.p. 250°/0.06 mm. TLC silica, ethyl acetate:isopropanol:water:0.88 ammonia (25:15:8:2) Rf 0.65.

EXAMPLE 34

1-Methyl-N$^5$-[3-[3-(aminomethyl)phenoxy]propyl]-1H-1,2,4-triazole-3,5-diamine

2-[[3-[3-[(3-Amino-1-methyl-1H-1,2,4-triazol-5-yl)amino]propoxy]phenyl]methyl]-1H-isoindole-1,3-(2H)-dione A mixture of potassium phthalimide (5.58 g) and 3-[3-[[3-amino-1-methyl-1H-1,2,4-triazol-5-yl]amino]-propoxy]N,N,N-trimethylbenzenemethanium iodide (6.69 g) in dimethylformamide was heated at 140°–160° for 6 h. The solvent was evaporated and the residue was dissolved in water and extracted with ethyl acetate. Evaporation of the organic extract gave an oil which was purified by column chromatography using methanol/acetone 1:9 as eluant to give the title compound as a white solid (2.3 g) m.p. 55°–57° TLC silica methanol/acetone; 1:9, Rf 0.42.

1-Methyl-N$^5$-[3-[3-(aminomethyl)phenoxy]propyl]-1H-1,2,4-triazole-3,5-diamine A solution of 2-[[3-[3-[(3-amino-1-methyl-1H-1,2,4-triazol-5-yl)amino]propoxy]phenyl]methyl]-1H-isoindole-1,3-(2H)-dione (1.62 g) and hydrazine hydrate (0.22 g) in ethanol (10 ml) was heated at reflux for 1.5 h. The solvent was evaporated and the residue was dissolved in dilute hydrochloric acid and filtered. The filtrate was basified with sodium carbonate, evaporated to dryness and extracted with hot isopropanol to give an oil which was purified by column chromatography using methanol/0.88 ammonia 79:1 as eluant to give the title compound as a crystalline solid (0.79 g) TLC silica, methanol/0.88 ammonia 79:1 Rf 0.5 NMR (d$_4$ MeOH) 2.77 t (1H); 3.0–3.3 m (3H); 5.95 t (2H); 6.30 s (2H); 6.57 q (2H); 6.65 s (3H); 7.95 m (2H).

EXAMPLE 35

Pharmaceutical Compositions (a) Tablets

|  | mg/tablet | mg/tablet |
|---|---|---|
| Active ingredient | 20.0 | 40.0 |
| Microcrystalline cellulose BPC | 99.5 | 199.0 |
| Magnesium stearate B.P. | 0.5 | 1.0 |
| Compression weight | 120.0 | 240.0 |

The drug is sieved through a 250 μm sieve, blended with the excipients and compressed using 6.5 mm and 8.0 mm diameter punches for the 20 and 40 mg strengths respectively. Tablets of other strengths may be prepared by increasing the compression weight and using punches to suit.

The tablets may be film coated with suitable film forming materials, e.g. methyl cellulose, ethyl cellulose or hydroxypropylmethyl cellulose, using standard techniques. Alternatively the tablets may be sugar coated.

(b) Capsules

|  | mg/capsule |
|---|---|
| Active ingredient | 20.0 |
| **Sta-Rx 1500 Starch | 79.5 | tuted by hydroxy or $C_{1-3}$ alkoxy, $C_{3-6}$ alkenyl, phenyl $C_{1-6}$ alkyl or pyridyl $C_{1-6}$ alkyl.

2. A compound according to claim 1 or a physiologically acceptable acid addition salt thereof, in which
$R_1$ and $R_2$, which may be the same or different, each represent hydrogen, $C_{1-6}$ alkyl, $C_{3-8}$ cycloalkyl, $C_{3-6}$ alkenyl, ar$C_{1-6}$alkyl wherein the aryl portion is phenyl or phenyl substituted with one or more $C_{1-3}$ alkyl or $C_{1-3}$ alkoxy groups or halogen atoms; or $C_{1-6}$ alkyl substituted by $C_{1-6}$ alkoxy, $C_{1-6}$ alkylamino or di$C_{1-6}$alkylamino;
Alk represents a straight or branched alkylene chain of 1 to 6 carbon atoms;
Q represents a furan or thiophen ring in which incorporation into the rest of the molecule is through bonds at the 2- and 5-positions, the furan ring optionally bearing a further substituent $R_7$ adjacent to the group $R_1R_2N$—Alk—, or Q represents a benzene ring in which incorporation into the rest of the molecule is through bonds at the 1- and 3-positions;
$R_7$ represents $C_{1-4}$ alkyl which may be substituted by hydroxy or $C_{1-4}$ alkoxy;
X represents —$CH_2$—, —O— or —S—;
n represents zer, 1 or 2;
m represents 2, 3 or 4;
$R_3$ represents hydrogen, $C_{1-6}$ alkyl, $C_{3-6}$ alkenyl, hydroxyalkyl having from two to six carbon atoms, $C_{1-6}$ alkoxy$C_{1-6}$alkyl, aryl or ar$C_{1-6}$alkyl, wherein aryl or the aryl portion of aralkyl is phenyl; and
$R_4$ and $R_5$, which may be the same or different, each represent hydrogen or $C_{1-6}$ alkyl;
with the proviso that when Q represents a furan, substituted furan or thiophen ring system and X represents oxygen, n cannot be zero.

3. A compound according to claim 1 in which when X represents an oxygen atom or

and n is zero, then Q only represents a benzene ring.

4. A compound according to claim 1 in which the total of m+n is 3 or 4.

5. A compound according to claim 4 in which the total of m+n is 3.

6. A compound according to claim 1 in which X is sulphur, n is 1 and m is 2.

7. A compound according to claim 1 in which X is oxygen or

n is zero and m is 3 or 4.

8. A compound according to claim 1 in which Q is a furan ring optionally substituted by the group $R_7$, where $R_7$ represents $C_{1-3}$ alkyl optionally substituted by $C_{1-4}$ alkoxy, or is a benzene ring in which incorporation into the rest of the molecule is through bonds at the 1- and 3- or 1- and 4-positions.

9. A compound according to claim 1 in which Alk represents a methylene, ethylene or propylene group.

10. A compound according to claim 1 in which $R_1$ represents hydrogen or $C_{1-4}$ alkyl and $R_2$ represents $C_{3-5}$ alkenyl or alkynyl, $C_{5-7}$ cycloalkyl, benzyl, $C_{1-6}$ alkyl, or $C_{1-4}$ alkyl substituted by $C_{1-3}$ alkoxy, hydroxy, di$C_{1-3}$ alkylamino or trifluoromethyl.

11. A compound according to claim 1 in which $R_3$ represents hydrogen or $C_{1-4}$ alkyl or hydroxy $C_{2-6}$ alkyl.

12. A compound according to claim 1 in which $R_4$ represents hydrogen or $C_{1-5}$ alkyl optionally substituted by a phenyl, pyridyl, hydroxy or $C_{1-3}$ alkoxy group and $R_5$ represents hydrogen or $C_{1-3}$ alkyl.

13. A compound according to claim 1 in which Q represents a furan or substituted furan ring, Alk represents a methylene group, $R_1$ and $R_2$ both represent $C_{1-3}$ alkyl groups and when present $R_7$ represents a $C_{1-3}$ alkyl group optionally substituted by a $C_{1-3}$ alkoxy group, n is 1, X is sulphur and m is 2.

14. A compound according to claim 1 in which Q represents a benzene ring, Alk represents a methylene, ethylene or propylene group; n is zero; X is oxygen or NH; m is 3 or 4; $R_1$ represents hydrogen or $C_{1-4}$ alkyl; $R_2$ represents a straight chain $C_{1-7}$ alkyl group which may be branched by a methyl group, or a $C_{1-4}$ alkyl group substituted by a di($C_{1-3}$) alkylamino, $C_{1-3}$ alkoxy, trifluoromethyl or phenyl group or $R_2$ represents a $C_{5-7}$ cycloalkyl group, or a $C_{3-5}$ alkenyl group; $R_3$ is hydrogen or $C_{1-2}$ alkyl or hydroxyethyl; $R_4$ represents hydrogen or $C_{1-3}$ alkyl optionally substituted by a phenyl or pyridyl group and $R_5$ represents hydrogen or $C_{1-3}$ alkyl.

15. A compound according to claim 1 which is:
1-methyl-$N^5$-[3-[3-[(dimethylamino)methyl]phenoxy]propyl]-1H-1,2,4-triazole-3,5-diamine
1-methyl-$N^5$-[2-[[[5-(dimethylamino)methyl-4-methyl-2-furanyl]methyl]thio]ethyl]-1H-1,2,4-triazole-3,5-diamine
1-methyl-$N^5$-[3-[3-[(dimethylamino)ethyl]phenoxy]propyl]-1H-1,2,4-triazole-3,5-diamine
1-methyl-$N^5$-[3-[3-[(1-propylamino)methyl]phenoxy]propyl]-1H-1,2,4-triazole-3,5-diamine
1-methyl-$N^5$-[2-[[4-methoxymethyl-5-[(dimethylamino)methyl]-2-furanylmethyl]thio]ethyl]-1H-1,2,4-triazole-3,5-diamine
1-methyl-$N^5$-[3-[4-[3-(dimethylamino)propyl]phenoxy]propyl]-1H-1,2,4-triazole-3,5-diamine
1-methyl-$N^5$-[3-[3-[(cyclohexylamino)methyl]phenoxy]propyl]-1H-1,2,4-triazole-3,5-diamine
1-methyl-$N^5$-[3-[3-[(2-propen-1-amino)methyl]phenoxy]propyl]-1H-1,2,4-triazole-3,5-diamine
1-methyl-$N^5$-[3-[3-[(heptylamino)methyl]phenoxy]propyl]-1H-1,2,4-triazole-3,5-diamine
1-methyl-$N^5$-[3-[3-[(2-methylpropylamino)methyl]phenoxy]propyl]-1H-1,2,4-triazole-3,5-diamine
1-methyl-$N^5$-[3-[3-[(2,2,2-trifluoroethylamino)methyl]phenoxy]propyl]-1H-1,2,4-triazole-3,5-diamine
1-methyl-$N^5$-[3-[3-[(butylmethylamino)methyl]phenoxy]propyl]-1H-1,2,4-triazole-3,5-diamine
1-(2-hydroxyethyl)-$N^5$-[3-[3-[(dimethylamino)methyl]phenoxy]propyl]-1H-1,2,4-triazole-3,5-diamine
or a physiologically acceptable acid addition salt thereof.

16. A compound according to claim 1, in which Q represents a furan or substituted furan ring, Alk represents a methylene group, $R_1$ and $R_2$ both represent $C_{1-3}$alkyl groups and when present $R_7$ represents a $C_{1-3}$ alkyl group optionally substituted by a $C_{1-3}$ alkoxy group, n is 1, X is sulphur, m is 2, $R_3$ is methyl and $R_4$ and $R_5$ are hydrogen.

17. A pharmaceutical composition for the treatment of conditions mediated through $H_2$-receptors comprising an effective amount of at least one compound as

-continued

| | mg/capsule |
|---|---|
| Magnesium Stearate B.P. | 0.5 |
| Fill Weight | 100.0 |

**A form of directly compressible starch supplied by Colorcon Ltd., Orpington, Kent.

The active ingredient is sieved through a 250 μm sieve and blended with the other materials. The mix is filled into No. 3 hard gelatin capsules using a suitable filling machine. Other doses may be prepared by increasing the fill weight and if necessary changing the capsule size to accommodate the increase.

(c) Sustained Release Tablets

| | mg/tablet |
|---|---|
| Active ingredient | 80 |
| *Cutina HR | 25 |
| Lactose B.P. | 142.5 |
| Magnesium Stearate B.P. | 2.5 |
| Compression weight | 250.0 |

*Cutina HR is a grade of microfine hydrogenated castor oil supplied by Sipon Products Ltd. London.

The drug is sieved through a 250 μm sieve and blended with the Cutina HR and lactose. The mixed powders are moistened with Industrial Methylated Spirits 74 O.P., granules are made, dried, screened and blended with the magnesium stearate. The lubricated granules are compressed using 8.5 mm punches to produce tablets with a hardness of not less than 10 Kp (Schleuniger tester).

(d) Injection for Intravenous Administration

| | % w/v |
|---|---|
| Active ingredient | 0.25 |
| Water for Injections BP to | 100.00 |

Sodium chloride may be added to adjust the tonicity of the solution and the pH may be adjusted to that of maximum stability using either dilute acid or alkali.

The solution is prepared, clarified and filled under nitrogen into appropriate sized ampoules sealed by fusion of the glass. The injection is sterilised by heating in an autoclave using one of the acceptable cycles. Alternatively the solution may be sterilised by filtration and filled into sterile ampoules under aseptic conditions.

(e) Syrup

| | mg/5 ml dose |
|---|---|
| Active ingredient | 20.0 mg |
| Sucrose | 2750.0 mg |
| Glycerine | 500.0 mg |
| Buffer | |
| Flavour | |
| | as necessary |
| Colour | |
| Preservative | |
| Distilled water | to 5.0 ml |

The active ingredient, buffer, flavour, preservative and colour are dissolved in some of the water. The remainder of the water is heated to approximately 80° C. and the sucrose is dissolved in this and cooled. The two solutions are mixed, adjusted to volume and clarified by filtration.

(f) Cream

A 1% cream may be prepared by dispersing the finely divided active ingredient in either of the two formulae for Cetamacrogol Cream B.P.C.

(g) Ointment

| | % w/w |
|---|---|
| Active ingredient | 1.0 |
| Propylene glycol | 5.0 |
| White soft paraffin | to 100.0 |

The finely divided active ingredient is suspended in the propylene glycol and this is dispersed in the molten soft paraffin. The mixture is stirred until cool.

We claim:

1. A compound of the formula (I)

$$R_1R_2N-Alk-Q(CH_2)_nX(CH_2)_mNH-\underset{N}{\overset{R_3}{\underset{|}{\diagdown}}}\underset{N}{\overset{N}{\diagup}}-NR_4R_5$$

and physiologically acceptable acid addition salts thereof, in which $R_1$ and $R_2$, which may be the same or different, each represent hydrogen, $C_{1-10}$ alkyl, $C_{3-8}$ cycloalkyl, $C_{3-6}$ alkenyl, $C_{3-6}$ alkynyl, $arC_{1-6}$alkyl, wherein the aryl portion is phenyl or phenyl substituted with one or more $C_{1-3}$ alkyl or $C_{1-3}$ alkoxy groups or halogen atoms; trifluoro$C_{1-6}$alkyl or $C_{1-6}$ alkyl substituted by hydroxy, $C_{1-6}$ alkoxy, amino, $C_{1-6}$ alkylamino, di$C_{1-6}$alkylamino or $C_{3-8}$ cycloalkyl;

Alk represents a straight or branched alkylene chain of 1 to 6 carbon atoms;

Q represents a furan or thiophen ring in which incorporation into the rest of the molecule is through bonds at the 2- and 5-positions, the furan ring optionally bearing a further substituent $R_7$ adjacent to the group $R_1R_2N$—Alk—, or Q represents a benzene ring in which incorporation into the rest of the molecule is through bonds at the 1- and 3- or 1- and 4-positions;

$R_7$ represents halogen or $C_{1-4}$ alkyl which may be substituted by hydroxy or $C_{1-4}$ alkoxy;

X represents —$CH_2$—, $$-\underset{\underset{R_6}{|}}{N}-,$$

—O— or —S— where $R_6$ represents hydrogen or methyl;

n represents zero, 1 or 2;

m represents 2, 3 or 4;

$R_3$ represents hydrogen, $C_{1-6}$ alkyl, $C_{3-6}$ alkenyl, phenyl $C_{1-6}$ alkyl, hydroxyalkyl having from two to six carbon atoms, $C_{1-6}$ alkoxy$C_{1-6}$alkyl, phenyl or phenyl substituted with one or more $C_{1-3}$ alkyl or $C_{1-3}$ alkoxy groups or halogen atoms; and $R_4$ and $R_5$, which may be the same or different, each represent hydrogen, $C_{1-6}$ alkyl, $C_{1-6}$ alkyl substidefined in claim 1 together with at least one pharmaceutically acceptable carrier or diluent.

18. A pharmaceutical composition according to claim 17 in which the active compound is in the form of a salt.

19. A pharmaceutical composition as claimed in claim 18 in which the salt is a hydrochloride, hydrobromide, sulphate, acetate, maleate, succinate, citrate or fumarate.

20. A pharmaceutical composition as claimed in claim 17 in the form of tablets, capsules or a syrup.

21. A method of treating a condition mediated through histamine $H_2$-receptors which comprises administering to a patient an effective amount of a compound as defined in claim 1 to relieve said condition.

* * * * *